United States Patent
Bateman

(10) Patent No.: US 9,880,129 B2
(45) Date of Patent: Jan. 30, 2018

(54) MASS SPECTROMETER

(75) Inventor: Robert Harold Bateman, Knutsford (GB)

(73) Assignee: MICROMASS UK LIMITED, Wilmslow (GB)

( * ) Notice: Subject to any disclaimer, the term of this patent is extended or adjusted under 35 U.S.C. 154(b) by 3372 days.

(21) Appl. No.: 11/568,167

(22) PCT Filed: Apr. 20, 2005

(86) PCT No.: PCT/GB2005/001488
§ 371 (c)(1),
(2), (4) Date: Oct. 3, 2007

(87) PCT Pub. No.: WO2005/104182
PCT Pub. Date: Nov. 3, 2005

(65) Prior Publication Data
US 2011/0095175 A1    Apr. 28, 2011

Related U.S. Application Data

(60) Provisional application No. 60/584,476, filed on Jul. 2, 2004.

(30) Foreign Application Priority Data

Apr. 20, 2004    (GB) .................................. 0408751.6

(51) Int. Cl.
*H01J 49/06*    (2006.01)
*G01N 27/62*    (2006.01)

(52) U.S. Cl.
CPC .......... *G01N 27/624* (2013.01); *H01J 49/062* (2013.01)

(58) Field of Classification Search
CPC .......... H01J 49/004; H01J 49/34; H01J 49/40; H01J 49/42; H01J 49/062; G01N 27/624
(Continued)

(56) References Cited

U.S. PATENT DOCUMENTS 5,905,258 A    5/1999  Clemmer et al.
6,040,575 A *  3/2000  Whitehouse et al. ........ 250/288
(Continued)

FOREIGN PATENT DOCUMENTS

EP    0253155    6/1987
EP    1365438    11/2003
(Continued)

OTHER PUBLICATIONS

Guevremont et al., *Atmospheric Pressure Ion Trapping in a Tandem FAIMS-FAIMS Coupled to a TOFMS: Studies with Electrospray Generated Gramicidin S Ions*, Journal American Society for Mass Spectrometry, No. 12, pp. 1320-1330, 2001.
(Continued)

*Primary Examiner* — David E Smith
(74) *Attorney, Agent, or Firm* — Womble Bond Dickinson (US) LLP; Deborah M. Vernon; Heath T. Misley

(57) ABSTRACT

A mass spectrometer is disclosed comprising a FAIMS device comprising two parallel electrodes (9a, 9b) in series with an ion mobility separator (12) forming part of a mass spectrometer. Ions are separated in the FAIMS device (9a, 9b) according to their rate of change of ion mobility with electric field strength. The ions which are onwardly transmitted from the FAIMS device (9a, 9b) are then passed to an ion separator device (12) comprising a plurality of electrodes (12) and an optional ion trapping region (33). Ions are radially confined with the ion separator by application of an AC or RF voltage to the electrodes (12) and ions are separated according to their ion mobility by applying an axial DC voltage gradient which may remain constant as a function of time or which may vary with time.

47 Claims, 8 Drawing Sheets

(58) Field of Classification Search
USPC .................................. 250/286–287, 290–293
See application file for complete search history.

(56) References Cited

U.S. PATENT DOCUMENTS

| | | | |
|---|---|---|---|
| 2002/0000811 A1 | 1/2002 | Koo et al. | |
| 2002/0014586 A1 | 2/2002 | Clemmer | |
| 2002/0070338 A1* | 6/2002 | Loboda .......................... | 250/287 |
| 2003/0089847 A1* | 5/2003 | Guevremont ........ | G01N 27/624 |
| | | | 250/282 |
| 2003/0222211 A1* | 12/2003 | Okumura .............. | H01J 49/004 |
| | | | 250/287 |
| 2004/0031920 A1* | 2/2004 | Giles et al. ................... | 250/287 |

FOREIGN PATENT DOCUMENTS

| | | |
|---|---|---|
| JP | 50-33895 | 4/1975 |
| JP | 8054373 | 2/1996 |
| JP | 2001503195 | 3/2001 |
| JP | 2005503195 | 2/2005 |
| JP | 2005513414 | 5/2005 |
| WO | 01/069218 | 9/2001 |
| WO | 01/069221 | 9/2001 |
| WO | 02/07185 | 1/2002 |

OTHER PUBLICATIONS

Notification of Reason(s) for Rejection for Japanese Patent Application No. 2007-508963, dated Feb. 22, 2011.

* cited by examiner

US 9,880,129 B2

MASS SPECTROMETER

CROSS REFERENCE TO RELATED APPLICATIONS

This application is the National Stage of International Application No. PCT/GB05/01488, filed on Apr. 20, 2005, which claims priority to and benefit of Provisional Patent Application Ser. No. 60/584,476, filed on Jul. 2, 2004, and priority to and benefit of United Kingdom Patent Application No. 0408751, filed Apr. 20, 2004. The entire contents of these applications are incorporated herein by reference.

BACKGROUND OF THE INVENTION

The present invention relates to an apparatus for separating ions, an ion mobility separator or spectrometer, a mass spectrometer, a method of separating ions and a method of mass spectrometry.

Ion mobility separation or ion mobility spectrometry is a method which may be used to separate ionic species at atmospheric pressures. The method may also be used at sub-atmospheric pressures provided that the mean free path of an ion in an ion mobility separator or ion mobility spectrometer is sufficiently small such that gas flow is viscous and not molecular.

Ion mobility spectrometers are used as analytical detectors and have a number of different applications. Ion mobility spectrometers are sometimes used, for example, for explosive and chemical warfare agent detection. Airports, for example, may use ion mobility spectrometers for detecting explosives and some government agencies carry ion mobility spectrometers on raids for on-site identification of drugs of abuse. On-site monitoring of pesticides, chemical warfare agents and industrial chemicals is another application for ion mobility spectrometers.

Ion mobility separators may be used to rapidly separate complex biological mixtures prior to analysis by mass spectrometry.

A known ion mobility spectrometer comprises an ion source, an ion gate, a drift tube and an ion detector. A sample to be analysed is ionised in the ion source and is then passed or transmitted to or passed to the ion gate. The ion gate is then pulsed ON and OFF to allow short pulses of ions to be emitted into the drift tube. The drift tube comprises a plurality of electrodes arranged along the length of the drift tube. A relatively high strength DC electric field is maintained along the length of the drift tube in order to propel or urge ions along and through the drift tube against a counterflow of gas. A gas inlet is provided adjacent to the drift tube exit region and a gas outlet is provided adjacent to the drift tube entrance region. Gas is arranged to flow through the drift tube in the opposite direction to the direct of travel of the ions. The drift gas flow rate may be varied in order to change the ionization spectra to alter selectivity.

Packets of ions are propelled from the ionisation region through the drift tube of the ion mobility spectrometer to the ion detector which is arranged at the exit region of the drift tube. Ions become separated within the drift region according to their ion mobility as they are urged against the counter flow of gas. The electric field is used to drag, propel or urge the ions through or against the drift gas which is sufficiently dense that the ions rapidly reach a terminal velocity. The terminal velocity is to a first approximation proportional to the strength of the applied electric field. The terminal velocity is also proportional to the mobility of the ion. Accordingly, ions can be separated from one another according to their ion mobility. The ion mobility of an ion is generally closely related to its cross sectional area and its charge.

Ionisation sources for ion mobility spectrometers of samples in the gaseous phase include radioactive nickel, Atmospheric Pressure Chemical Ionisation ion sources and photoionisation ion sources. More recently ion mobility spectrometry of polar samples in liquid solution has become possible using Electrospray Ionization ("ESI").

Ion mobility spectrometers provide simple, inexpensive, high throughput screening under ambient conditions.

More recently a variation of a conventional ion mobility spectrometer has been developed known as a Field Asymmetric Ion Mobility Spectrometry ("FAIMS") device. FAIMS devices differ from conventional ion mobility spectrometers in that ions of different species are separated within a FAIMS device according to their rate of change of ion mobility with electric field strength rather than their ion mobility per se. FAIMS devices are capable of separating gas-phase ions at atmospheric pressures and ambient temperatures but can also be operated over a wide range of pressures and temperatures.

Field Asymmetric Ion Mobility Spectrometry devices typically utilise relatively strong or high periodic electric fields which may, for example, have a field strength of approximately 10,000 V/cm. The periodic electrical fields or waveforms which are used to separate ions are asymmetric i.e. there is a difference between the magnitude of the peak positive voltage and the magnitude of the peak negative voltage of the applied electric field or waveform. Either the peak positive or the peak negative voltage may be the higher.

Field Asymmetric Ion Mobility Spectrometry devices utilise an electric field to drag or propel ions through a gas that is sufficiently dense such that the ions rapidly reach a terminal velocity. The terminal velocity is approximately proportional to the strength of the electric field. However, this proportionality changes at high electric field strengths and is also compound-dependent. Accordingly, the compound specific variation in ion mobility with electric field strength can be used to separate ions from each other.

The rate of change of ion mobility with change in electric field strength is not currently believed to be directly related to the mobility of the ion. The change of mobility with electric field strength is not currently very well understood and is generally considered to be largely unpredictable. It is possible that the rate of change of ion mobility is dependent upon the susceptibility of an ion to distort in the presence of a strong electric field.

A known FAIMS device comprises two metal plates or electrodes. An asymmetric voltage or potential is applied to the metal plates or electrodes such that a time varying asymmetric electric field is generated between the metal plates or electrodes. If a mixture of ions of different sizes and types is introduced between the two metal plates or electrodes, then the application of an appropriate asymmetric voltage waveform to the plates or electrodes will create a condition wherein some types of ion will tend to drift towards and hit one of the metal plates or electrodes whilst other types of ion will tend to remain located between the plates or electrodes. The asymmetric voltage waveform may, for example, comprise a square wave wherein a relatively high positive voltage is applied for a relatively short period of time and a relatively low negative voltage is applied for a relatively long period of time (or vice versa).

If the electric field which is created by the application of the asymmetric voltage or waveform is relatively weak (e.g. if the electric field strength is less than 200 V/cm) then ions will tend to move back and forth, or otherwise oscillate between the plates or electrodes, during the application of the asymmetric voltage waveform. The ions will not tend to move towards either plate or electrode. If, however, the electric field which is created during a high-voltage part of the asymmetric voltage or waveform is relatively strong or high (e.g. if the electric field strength exceeds, for example, about 5000 V/cm) then the ions will then tend to drift towards one or other of the plates or electrodes.

An ion will drift towards a plate or electrode due to the fact that the mobility of the ion during the application of a relatively high strength electric field is different to the mobility of the ion during the application of a relatively low strength electric field. Since the mobility of the ion defines how fast the ion moves in an electric field, the ion will move proportionately farther in a relatively high strength electric field than the ion will move in a relatively low strength electric field (or vice versa).

The asymmetric voltage waveform which is typically applied tends to have a relatively high frequency e.g. ≥200 kHz. The small extra distance travelled during each high-voltage period of a voltage waveform results in a net drift of the ion towards one of the plates.

Some ions exhibit a mobility which increases with electric field strength whilst other ions exhibit a mobility which decreases with electric field strength. As a result different ions can travel in opposite directions between the plates or electrodes during the application of an asymmetric voltage waveform. Certain ions, for example, such as the chloride ion in nitrogen or oxygen gas experience very large changes in mobility as a function of electric field strength. During the application of an asymmetric waveform, chloride ions will therefore drift very rapidly towards a plate or electrode. On the other hand, some ions, such as the tetrapropylammonium ion exhibit only a very small relative change in ion mobility with electric field strength and hence will tend to drift only very slowly towards one of the plates or electrodes.

The relative or net drift of an ion towards one of the metal plates or electrodes can be stopped or otherwise counterbalanced by applying a small compensation DC voltage to one of the plates or electrodes. If the compensation voltage is arranged to have a specific magnitude and polarity then specific species of ions can be arranged to experience an electric force which counteracts the force on the ion towards one of the plates or electrodes. As a result the overall net drift of the ion towards one of the plates or electrodes will be zero. The voltage that is applied in order to reverse or compensate for the ion drift is commonly known as the compensation voltage ("CV").

The compensation voltage necessary to stop or counteract the drift of a chloride ion will be relatively high since the mobility of chloride ions increases significantly at high electric field strengths. On the other hand, the compensation voltage necessary to stop or counteract the drift of tetrapropylammonium ions will be relatively small. It is therefore apparent that by appropriate selection and setting of the compensation voltage certain ions can be selected to experience zero net force (and hence will be transmitted through the FAIMS device without impinging upon the plates or electrodes) whilst the majority of other ions will experience a non-zero net force and hence will tend to collide with one of the plates or electrodes and hence become lost to the system.

If a mixture of ions is placed between the two plates or electrodes of a FAIMS device and a high voltage asymmetric waveform is applied to the plate or electrodes, then different types of ions will begin to migrate towards the plates or electrodes at rates which are characteristic of those ions. If a specific DC compensation voltage is also applied to the plates or electrodes then most ions will hit the plates whilst some ions for which the compensation voltage is exactly the right voltage to provide an electric force which counter balances or compensates for the drift caused by the application of the asymmetric waveform will not drift towards the plates or electrodes. These ions will instead emerge from the FAIMS device. A complex mixture of ions can therefore become separated by using a FAIMS device. The types of ion that are in a balanced or equilibrium condition between the plates or electrodes of a FAIMS device can be selected or varied by adjusting the DC compensation voltage applied to the plates or electrodes.

A mixture of ions carried by a gas flow in a FAIMS device can be resolved into several peaks by scanning (i.e. varying) the DC compensation voltage and simultaneously detecting the ions successfully transported through the gap between the plates or electrodes. Different types of ion will travel or pass between the plates or electrodes at different specific characteristic DC compensation voltages. The spectrum of peaks observed in this manner is referred to as a compensation voltage spectrum.

An alternative known Field Asymmetric Ion Mobility Spectrometry device comprises two concentric cylindrical electrodes instead of two planar electrodes. An asymmetric voltage waveform and a DC compensation voltage are applied to the inner and outer cylindrical electrodes. If the polarity of the asymmetric waveform is such that a specific ion species is caused to drift towards the inner cylindrical electrode in the absence of a compensation voltage, then the application of an appropriate DC compensation voltage can be arranged so as to introduce an additional force which repels the ion away from the inner cylindrical electrode. The drift towards an electrode is therefore counterbalanced by a compensation electric field which will balance at a certain radial distance. If the ion is nearer to the inner cylindrical electrode then it will migrate away from the inner cylindrical electrode to a radial position wherein the compensation field is balanced. Similarly, if the ion is nearer to the outer cylindrical electrode then it will migrate away from the outer cylindrical electrode towards a radial position wherein the compensation field is balanced. As a result different species of ions become focused at different fixed radial positions between the two concentric cylindrical electrodes. The ions are distributed around an ideal or theoretical radial position due to diffusion, space charge ion-ion repulsion and gas turbulence/movement effects.

A similar focusing effect can be obtained with concentric spheres. Another known Field Asymmetric Ion Mobility Spectrometry device comprises two concentric cylindrical electrodes which terminate as two concentric hemispherical sections at one end. This arrangement can be used to further concentrate specific ions at one end of the FAIMS device.

Known ion mobility spectrometers or separators suffer from a relatively poor resolution in that known ion mobility spectrometers or separators can only separate ions of different mobilities with a relatively low or poor resolution of e.g. typically 1 part in 20 and at best 1 part in 50. Factors that determine the resolution of known ion mobility spectrometers or separators include the initial ion pulse width, the broadening due to Coulomb repulsion between ions in both the ionization and drift regions, the spatial broadening due to diffusion of ion packet and the ion-molecule reactions in the drift region. The Coulomb contribution to the resolution depends on the total number of ions initially generated.

For some applications the low resolution inherent with known ion mobility spectrometers or separators is too low and can lead to false positives. For example, if an ion mobility spectrometer is used to detect chemicals used in explosives, or bio-chemicals used as nerve agents in weapons of mass destruction, then another unrelated chemical that may be present may be detected and mistaken for a targeted chemical reagent.

Similarly, known Field Asymmetric Ion Mobility Spectrometry devices also suffer from relatively poor resolution i.e. they are capable of separating ions of different mobility susceptibility to field strength to only typically 1 part in 20 or at best 1 part in 50. For some applications this relatively low resolution can also lead to false positives.

SUMMARY OF THE INVENTION

According to an aspect of the present invention there is provided apparatus comprising:

a first device for separating ions according to their ion mobility or according to their rate of change of ion mobility with electric field strength; and a second separate device for separating ions according to their ion mobility or according to their rate of change of ion mobility with electric field strength, the second device being arranged downstream of the first device.

The first device is preferably arranged to separate ions according to their rate of change of ion mobility with electric field strength. According to the preferred embodiment the first device comprises a Field Asymmetric Ion Mobility Spectrometry ("FAIMS") device.

The first device may comprise at least a first electrode and a second electrode and wherein ions are arranged to be received, in use, between the first and second electrodes. In an embodiment the first electrode comprises a first planar plate or planar electrode and the second electrode comprises a second planar plate or planar electrode. In another embodiment the first electrode comprises an inner cylindrical electrode and the second electrode comprise an outer concentric cylindrical electrode. According to an embodiment the first electrode may terminate in a hemispherical section and/or the second electrode may terminate in a hemispherical section. Means for providing a flow of gas, wherein the flow of gas directs or urges ions to pass through the first device is preferably provided.

An asymmetric periodic voltage waveform is preferably applied to the first device, wherein the asymmetric periodic voltage waveform has a peak positive voltage and a peak negative voltage. The peak positive voltage preferably has an amplitude selected from the group consisting of: (i) <100 V; (ii) 100-500 V; (iii) 500-1000 V; (iv) 1-2 kV; (v) 2-3 kV; (vi) 3-4 kV; (vii) 4-5 kV; (viii) 5-6 kV; (ix) 6-7 kV; (x) 7-8 kV; (xi) 8-9 kV; (xii) 9-10 kV; and (xiii) >10 kV. The peak negative voltage preferably has an amplitude selected from the group consisting of: (i) <100 V; (ii) 100-500 V; (iii) 500-1000 V; (iv) 1-2 kV; (v) 2-3 kV; (vi) 3-4 kV; (vii) 4-5 kV; (viii) 5-6 kV; (ix) 6-7 kV; (x) 7-8 kV; (xi) 8-9 kV; (xii) 9-10 kV; and (xiii) >10 kV.

The ratio of the amplitude of the peak positive voltage to the amplitude of the peak negative voltage or the ratio of the amplitude of the peak negative voltage to the amplitude of the peak positive voltage is preferably selected from the group consisting of: (i) <1.5; (ii) 1.5-1.75; (iii) 1.75-2; (iv) 2-2.25; (v) 2.25-2.5; (vi) 2.5-2.75; (vii) 2.75-3; (viii) 3-3.25; (ix) 3.25-3.5; (x) 3.5-4; (xi) 4-5; (xii) 5-10; and (xiii) >10.

The asymmetric periodic voltage waveform preferably generates an electric field having a maximum or average field strength selected from the group consisting of: (i) <10 V/cm; (ii) 10-50 V/cm; (iii) 50-100 V/cm; (iv) 100-500 V/cm; (v) 500-1000 V/cm; (vi) 1-2 kV/cm; (vii) 2-3 kV/cm; (viii) 3-4 kV/cm; (ix) 4-5 kV/cm; (x) 5-6 kV/cm; (xi) 6-7 kV/cm; (xii) 7-8 kV/cm; (xiii) 8-9 kV/cm; (xiv) 9-10 kV/cm; and (xv) >10 kV/cm.

A DC compensation voltage is preferably applied to the first device. The DC compensation voltage preferably has an amplitude selected from the group consisting of: (i) <5 V; (ii) 5-10 V; (iii) 10-15 V; (iv) 15-20 V; (v) 20-50 V; (vi) 50-100 V; and (vii) >100 V. The DC compensation voltage preferably acts to counterbalance or counteract a force which would otherwise cause desired ions to drift towards an electrode of the first device. The DC compensation voltage may be scanned preferably in a periodic, linear, non-linear, regular or irregular manner.

The first device is preferably arranged to be operated, in use, at a pressure selected from the group consisting of: (i) <0.0001 mbar; (ii) 0.0001-0.0005 mbar; (iii) 0.0005-0.001 mbar; (iv) 0.001-0.005 mbar; (v) 0.005-0.01 mbar; (vi) 0.01-0.05 mbar; (vii) 0.05-0.1 mbar; (viii) 0.1-0.5 mbar; (ix) 0.5-1 mbar; (x) 1-5 mbar; (xi) 5-10 mbar; (xii) 10-50 mbar; (xiii) 50-100 mbar; (xiv) 100-500 mbar; (xv) 500-1000 mbar; and (xvi) >1000 mbar.

The second device is preferably arranged to separate ions according to their ion mobility. The second device is preferably arranged to separate a group of ions received from the first device, wherein the group of ions has been separated from other ions on the basis of their rate of change of ion mobility with electric field strength. The second device preferably comprises an ion mobility separator or ion mobility spectrometer.

The second device preferably comprises a plurality of electrodes. The second device is preferably selected from the group consisting of: (i) an ion funnel comprising a plurality of electrodes having apertures therein through which ions are transmitted, wherein the diameter of the apertures becomes progressively smaller or larger; (ii) an ion tunnel comprising a plurality of electrodes having apertures therein through which ions are transmitted, wherein the diameter of the apertures remains substantially constant; and (iii) a stack of plate, ring or wire loop electrodes.

The second device preferably comprises a plurality of electrodes, each electrode having an aperture through which ions are transmitted in use. The second device preferably comprises a plurality of electrodes and wherein each electrode has a substantially circular aperture. The second device preferably comprises a plurality of electrodes and wherein each electrode has a single aperture through which ions are transmitted in use.

The diameter of the apertures of at least 10%, 20%, 30%, 40%, 50%, 60%, 70%, 80%, 90% or 95% of the electrodes forming the second device is preferably selected from the group consisting of: (i) less than or equal to 10 mm; (ii) less than or equal to 9 mm; (iii) less than or equal to 8 mm; (iv) less than or equal to 7 mm; (v) less than or equal to 6 mm; (vi) less than or equal to 5 mm; (vii) less than or equal to 4 mm; (viii) less than or equal to 3 mm; (ix) less than or equal to 2 mm; and (x) less than or equal to 1 mm.

The second device preferably comprises a plurality of electrodes and at least 10%, 20%, 30%, 40%, 50%, 60%, 70%, 80%, 90% or 95% of the electrodes forming the second device have apertures which are substantially the same size or area.

According to an alternative embodiment the second device preferably comprises a segmented rod set. The second device preferably consists of: (i) 10-20 electrodes; (ii)

20-30 electrodes; (iii) 30-40 electrodes; (iv) 40-50 electrodes; (v) 50-60 electrodes; (vi) 60-70 electrodes; (vii) 70-80 electrodes; (viii) 80-90 electrodes; (ix) 90-100 electrodes; (x) 100-110 electrodes; (xi) 110-120 electrodes; (xii) 120-130 electrodes; (xiii) 130-140 electrodes; (xiv) 140-150 electrodes; or (xv) more than 150 electrodes.

The second device preferably comprises a plurality of electrodes and wherein the thickness of at least 10%, 20%, 30%, 40%, 50%, 60%, 70%, 80%, 90% or 95% of the electrodes is selected from the group consisting of: (i) less than or equal to 3 mm; (ii) less than or equal to 2.5 mm; (iii) less than or equal to 2.0 mm; (iv) less than or equal to 1.5 mm; (v) less than or equal to 1.0 mm; and (vi) less than or equal to 0.5 mm.

The second device preferably has a length selected from the group consisting of: (i) less than 5 cm; (ii) 5-10 cm; (iii) 10-15 cm; (iv) 15-20 cm; (v) 20-25 cm; (vi) 25-30 cm; and (vii) greater than 30 cm.

The second device preferably comprises a plurality of electrodes wherein at least 60%, 65%, 70%, 75%, 80%, 85%, 90% or 95% of the electrodes comprise an aperture through which ions are transmitted in use.

The second device preferably comprises a plurality of electrodes and an AC or RF voltage is applied to at least some of the electrodes of the second device in order to confine at least some ions, in use, near to a central axis of the second device. The AC or RF voltage preferably has a frequency within a range selected from the group consisting of: (i) <0.1 MHz; (ii) 0.1-0.5 MHz; (iii) 0.5-1 MHz; (iv) 1-5 MHz; and (v) >5 MHz.

According to an embodiment one or more DC voltage gradients are preferably maintained across at least a portion of the second device.

According to an embodiment the second device comprises a drift tube comprising one or more electrodes and wherein one or more axial DC voltage gradients are maintained in use along at least a portion of the drift tube.

According to an embodiment the DC voltage gradient causes an electric field to be generated having a maximum or average field strength selected from the group consisting of: (i) <10 V/cm; (ii) 10-50 V/cm; (iii) 50-100 V/cm; (iv) 100-500 V/cm; (v) 500-1000 V/cm; (vi) 1-2 kV/cm; (vii) 2-3 kV/cm; (viii) 3-4 kV/cm; (ix) 4-5 kV/cm; (x) 5-6 kV/cm; (xi) 6-7 kV/cm; (xii) 7-8 kV/cm; (xiii) 8-9 kV/cm; (xiv) 9-10 kV/cm; and (xv) >10 kV/cm.

According to a particularly preferred embodiment the second device comprises a plurality of electrodes and wherein, in use, one or more transient DC voltages or one or more transient DC voltage waveforms are progressively applied to the electrodes so that at least some ions having a first ion mobility are separated from other ions having a second different ion mobility. The one or more transient DC voltages or the one or more transient DC voltage waveforms is preferably such that at least 10%, 20%, 30%, 40%, 50%, 60%, 70%, 80%, 90% or 95% of the ions having the first ion mobility are substantially moved along the second device by the one or more transient DC voltages or the one or more transient DC voltage waveforms as the one or more transient DC voltages or the one or more transient DC voltage waveforms are progressively applied to the electrodes.

According to an embodiment the one or more transient DC voltages or the one or more transient DC voltage waveforms are such that at least 10%, 20%, 30%, 40%, 50%, 60%, 70%, 80%, 90% or 95% of the ions having the second ion mobility are moved along the second device by the applied DC voltage to a lesser degree than the ions having the first ion mobility as the one or more transient DC voltages or the one or more transient DC voltage waveforms are progressively applied to the electrodes. Preferably, the one or more transient DC voltages or the one or more transient DC voltage waveforms are such that at least 10%, 20%, 30%, 40%, 50%, 60%, 70%, 80%, 90% or 95% of the ions having the first ion mobility are moved along the second device with a higher velocity than the ions having the second ion mobility.

According to an embodiment the second device comprises an ion mobility separator for separating ions according to their ion mobility, the ion mobility separator comprising a plurality of electrodes wherein in use one or more transient DC voltages or one or more transient DC voltage waveforms are progressively applied to the electrodes so that ions are moved towards a region of the ion mobility separator wherein at least one electrode has a potential such that at least some ions having a first ion mobility will pass across the potential whereas other ions having a second different ion mobility will not pass across the potential. Preferably, the one or more transient DC voltages or the one or more transient DC voltage waveforms are such that at least 10%, 20%, 30%, 40%, 50%, 60%, 70%, 80%, 90% or 95% of the ions having the first ion mobility pass across the potential. Preferably, the one or more transient DC voltages or the one or more transient DC voltage waveforms are such that at least 10%, 20%, 30%, 40%, 50%, 60%, 70%, 80%, 90% or 95% of the ions having the second ion mobility will not pass across the potential.

The at least one electrode is preferably provided with a voltage such that a potential hill or valley is provided. The one or more transient DC voltages or the one or more transient DC voltage waveforms are preferably such that at least 10%, 20%, 30%, 40%, 50%, 60%, 70%, 80%, 90% or 95% of the ions having the first ion mobility exit the second device substantially before ions having the second ion mobility.

According to an embodiment the one or more transient DC voltages or the one or more transient DC voltage waveforms are such that at least 10%, 20%, 30%, 40%, 50%, 60%, 70%, 80%, 90% or 95% of the ions having the second ion mobility exit the second device substantially after ions having the first ion mobility.

Preferably, a majority of the ions having the first ion mobility exit the second device a time t before a majority of the ions having the second ion mobility exit the second device, wherein t falls within a range selected from the group consisting of: (i) <1 µs; (ii) 1-10 µs; (iii) 10-50 µs; (iv) 50-100 µs; (v) 100-200 µs; (vi) 200-300 µs; (vii) 300-400 µs; (viii) 400-500 µs; (ix) 500-600 µs; (x) 600-700 µs; (xi) 700-800 µs; (xii) 800-900 µs; (xiii) 900-1000 µs; (xiv) 1.0-1.1 ms (xv) 1.1-1.2 ms; (xvi) 1.2-1.3 ms; (xvii) 1.3-1.4 ms; (xviii) 1.4-1.5 ms; (xix) 1.5-1.6 ms; (xx) 1.6-1.7 ms; (xxi) 1.7-1.8 ms; (xxii) 1.8-1.9 ms; (xxiii) 1.9-2.0 ms; (xxiv) 2.0-2.5 ms; (xxv) 2.5-3.0 ms; (xxvi) 3.0-3.5 ms; (xxvii) 3.5-4.0 ms; (xxviii) 4.0-4.5 ms; (xxix) 4.5-5.0 ms; (xxx) 5-10 ms; (xxxi) 10-15 ms; (xxxii) 15-20 ms; (xxxiii) 20-25 ms; (xxxiv) 25-30 ms; and (xxxv) >30 ms.

According to an embodiment the second device comprises an ion mobility separator for separating ions according to their ion mobility, the ion mobility separator comprising a plurality of electrodes wherein in use one or more transient DC voltages or one or more transient DC voltage waveforms are progressively applied to the electrodes so that:

(i) ions are moved towards a region of the ion mobility separator wherein at least one electrode has a first potential such that at least some ions having first and second different ion mobilities will pass across the first potential whereas other ions having a third different ion mobility will not pass across the first potential; and then (ii) ions having the first and second ion mobilities are moved towards a region of the ion mobility separator wherein at least one electrode has a second potential such that at least some ions having the first ion mobility will pass across the second potential whereas other ions having the second different ion mobility will not pass across the second potential.

Preferably, the one or more transient DC voltages or the one or more transient DC voltage waveforms and the first potential are such that at least 10%, 20%, 30%, 40%, 50%, 60%, 70%, 80%, 90% or 95% of the ions having the first ion mobility pass across the first potential. Preferably, the one or more transient DC voltages or the one or more transient DC voltage waveforms and the first potential are such that at least 10%, 20%, 30%, 40%, 50%, 60%, 70%, 80%, 90% or 95% of the ions having the second ion mobility pass across the first potential.

According to an embodiment the one or more transient DC voltages or the one or more transient DC voltage waveforms and the first potential are such that at least 10%, 20%, 30%, 40%, 50%, 60%, 70%, 80%, 90% or 95% of the ions having the third ion mobility do not pass across the first potential.

Preferably, the one or more transient DC voltages or the one or more transient DC voltage waveforms and the second potential are such that at least 10%, 20%, 30%, 40%, 50%, 60%, 70%, 80%, 90% or 95% of the ions having the first ion mobility pass across the second potential. Similarly, the one or more transient DC voltages or the one or more transient DC voltage waveforms and the second potential are preferably such that at least 10%, 20%, 30%, 40%, 50%, 60%, 70%, 80%, 90% or 95% of the ions having the second ion mobility do not pass across the second potential.

The one or more transient DC voltages or the one or more transient DC voltage waveforms are preferably such that at least 10%, 20%, 30%, 40%, 50%, 60%, 70%, 80%, 90% or 95% of the ions having the second ion mobility exit the ion mobility separator substantially before ions having the first and third ion mobilities.

According to an embodiment the one or more transient DC voltages or the one or more transient DC voltage waveforms are such that at least 10%, 20%, 30%, 40%, 50%, 60%, 70%, 80%, 90% or 95% of the ions having the first and third ion mobilities exit the ion mobility separator substantially after ions having the second ion mobility.

A majority of the ions having the second ion mobility preferably exit the ion mobility separator a time t before a majority of the ions having the first and third ion mobilities exit the ion mobility separator, wherein t falls within a range selected from the group consisting of: (i) <1 µs; (ii) 1-10 µs; (iii) 10-50 µs; (iv) 50-100 µs; (v) 100-200 µs; (vi) 200-300 µs; (vii) 300-400 µs; (viii) 400-500 µs; (ix) 500-600 µs; (x) 600-700 µs; (xi) 700-800 µs; (xii) 800-900 µs; (xiii) 900-1000 µs; (xiv) 1.0-1.1 ms (xv) 1.1-1.2 ms; (xvi) 1.2-1.3 ms; (xvii) 1.3-1.4 ms; (xviii) 1.4-1.5 ms; (xix) 1.5-1.6 ms; (xx) 1.6-1.7 ms; (xxi) 1.7-1.8 ms; (xxii) 1.8-1.9 ms; (xxiii) 1.9-2.0 ms; (xxiv) 2.0-2.5 ms; (xxv) 2.5-3.0 ms; (xxvi) 3.0-3.5 ms; (xxvii) 3.5-4.0 ms; (xxviii) 4.0-4.5 ms; (xxix) 4.5-5.0 ms; (xxx) 5-10 ms; (xxxi) 10-15 ms; (xxxii) 15-20 ms; (xxxiii) 20-25 ms; (xxxiv) 25-30 ms; and (xxxv) >30 ms.

According to an embodiment the one or more transient DC voltages applied to the second device create: (i) a potential hill or barrier; (ii) a potential well; (iii) a combination of a potential hill or barrier and a potential well; (iv) multiple potential hills or barriers; (v) multiple potential wells; or (vi) a combination of multiple potential hills or barriers and multiple potential wells. The one or more transient DC voltage waveforms preferably comprise a repeating waveform such as a square wave.

According to an embodiment the one or more transient DC voltage waveforms applied to the second device create a plurality of potential peaks or wells separated by intermediate regions. The DC voltage gradient in the intermediate regions is preferably non-zero e.g. the DC voltage gradient is positive or negative in the intermediate regions. Preferably, the DC voltage gradient in the intermediate regions is linear. Alternatively, the DC voltage gradient in the intermediate regions is non-linear. According to an embodiment the DC voltage gradient in the intermediate regions increases or decreases exponentially.

Preferably, the amplitude of the potential peaks or wells remains substantially constant. The amplitude of the potential peaks or wells may become progressively larger or smaller. The amplitude of the potential peaks or wells may increase or decrease either linearly or non-linearly.

According to an embodiment in use an axial DC voltage gradient is maintained along at least a portion of the length of the second device and wherein the axial voltage gradient varies with time.

Preferably, the second device comprises an ion mobility separator comprising a first electrode held at a first reference potential, a second electrode held at a second reference potential, and a third electrode held at a third reference potential, wherein:

at a first time $t_1$ a first DC voltage is supplied to the first electrode so that the first electrode is held at a first potential above or below the first reference potential;

at a second later time $t_2$ a second DC voltage is supplied to the second electrode so that the second electrode is held at a second potential above or below the second reference potential; and at a third later time $t_3$ a third DC voltage is supplied to the third electrode so that the third electrode is held at a third potential above or below the third reference potential.

According to an embodiment at the first time $t_1$ the second electrode is at the second reference potential and the third electrode is at the third reference potential;

at the second time $t_2$ the first electrode is at the first potential and the third electrode is at the third reference potential; and at the third time $t_3$ the first electrode is at the first potential and the second electrode is at the second potential.

According to an embodiment at the first time $t_1$ the second electrode is at the second reference potential and the third electrode is at the third reference potential;

at the second time $t_2$ the first electrode is no longer supplied with the first DC voltage so that the first electrode is returned to the first reference potential and the third electrode is at the third reference potential; and at the third time $t_3$ the first electrode is at the first reference potential the second electrode is no longer supplied with the second DC voltage so that the second electrode is returned to the second reference potential.

Preferably, the first, second and third reference potentials are substantially the same. The first, second and third DC voltages may be substantially the same. Preferably, the first, second and third potentials are substantially the same.

According to an embodiment the second device comprises an ion mobility separator comprising 3, 4, 5, 6, 7, 8, 9, 10, 11, 12, 13, 14, 15, 16, 17, 18, 19, 20, 21, 22, 23, 24, 25, 26, 27, 28, 29, 30 or >30 segments, wherein each segment comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or >30 electrodes and wherein the electrodes in a segment are maintained at substantially the same DC potential. A plurality of segments are preferably maintained at substantially the same DC potential. Each segment is preferably maintained at substantially the same DC potential as the subsequent nth segment, wherein n is 3, 4, 5, 6, 7, 8, 9, 10, 11, 12, 13, 14, 15, 16, 17, 18, 19, 20, 21, 22, 23, 24, 25, 26, 27, 28, 29, 30 or >30.

According to an embodiment ions are confined radially within the first device and/or the second device by an AC or RF electric field. Preferably, ions are radially confined within the first device and/or the second device in a pseudo-potential well and are moved axially by a real potential barrier or well.

According to an embodiment in use one or more AC or RF voltage waveforms are applied to at least some electrodes of the first device and/or the second device so that ions are urged along at least a portion of the length of the first device and/or the second device. Preferably, the transit time of ions through the first device and/or the second device is selected from the group consisting of: (i) less than or equal to 20 ms; (ii) less than or equal to 10 ms; (iii) less than or equal to 5 ms; (iv) less than or equal to 1 ms; and (v) less than or equal to 0.5 ms.

The second device is preferably maintained in use at a pressure selected from the group consisting of: (i) greater than or equal to 0.0001 mbar; (ii) greater than or equal to 0.0005 mbar; (iii) greater than or equal to 0.001 mbar; (iv) greater than or equal to 0.005 mbar; (v) greater than or equal to 0.01 mbar; (vi) greater than or equal to 0.05 mbar; (vii) greater than or equal to 0.1 mbar; (viii) greater than or equal to 0.5 mbar; (ix) greater than or equal to 1 mbar; (x) greater than or equal to 5 mbar; and (xi) greater than or equal to 10 mbar. Preferably, the second device is maintained in use at a pressure selected from the group consisting of: (i) less than or equal to 10 mbar; (ii) less than or equal to 5 mbar; (iii) less than or equal to 1 mbar; (iv) less than or equal to 0.5 mbar; (v) less than or equal to 0.1 mbar; (vi) less than or equal to 0.05 mbar; (vii) less than or equal to 0.01 mbar; (viii) less than or equal to 0.005 mbar; (ix) less than or equal to 0.001 mbar; (x) less than or equal to 0.0005 mbar; and (xi) less than or equal to 0.0001 mbar. Preferably, the second device is maintained, in use, at a pressure selected from the group consisting of: (i) between 0.0001 and 10 mbar; (ii) between 0.0001 and 1 mbar; (iii) between 0.0001 and 0.1 mbar; (iv) between 0.0001 and 0.01 mbar; (v) between 0.0001 and 0.001 mbar; (vi) between 0.001 and 10 mbar; (vii) between 0.001 and 1 mbar; (viii) between 0.001 and 0.1 mbar; (ix) between 0.001 and 0.01 mbar; (x) between 0.01 and 10 mbar; (xi) between 0.01 and 1 mbar; (xii) between 0.01 and 0.1 mbar; (xiii) between 0.1 and 10 mbar; (xiv) between 0.1 and 1 mbar; and (xv) between 1 and 10 mbar.

According to an embodiment the first device and/or the second device is maintained, in use, at a pressure such that a viscous drag is imposed upon ions passing through the first device and/or the second device. Preferably, in use one or more transient DC voltages or one or more transient DC voltage waveforms are initially provided at a first axial position and are then subsequently provided at second, then third different axial positions along the first device and/or the second device.

One or more transient DC voltages or one or more transient DC voltage waveforms preferably move from one end of the first device and/or the second device to another end of the first device and/or the second device so that at least some ions are urged along the first device and/or the second device. Preferably, one or more transient DC voltages or one or more transient DC voltage waveforms applied to electrodes of the first device and/or the second device have at least 2, 3, 4, 5, 6, 7, 8, 9 or 10 different amplitudes. The amplitude of one or more transient DC voltages or one or more transient DC voltage waveforms applied to electrodes of the first device and/or the second device preferably remain substantially constant with time. Alternatively, the amplitude of one or more transient DC voltages or one or more transient DC voltage waveforms applied to electrodes of the first device and/or the second device may vary with time. The amplitude of the one or more transient DC voltages or the one or more transient DC voltage waveforms may either: (i) increase with time; (ii) increase then decrease with time; (iii) decrease with time; or (iv) decrease then increase with time.

The first device and/or the second device may comprise an upstream entrance region, a downstream exit region and an intermediate region, wherein:

in the entrance region the amplitude of the one or more transient DC voltages or the one or more transient DC voltage waveforms has a first amplitude;

in the intermediate region the amplitude of the one or more transient DC voltages or the one or more transient DC voltage waveforms has a second amplitude; and in the exit region the amplitude of the one or more transient DC voltages or the one or more transient DC voltage waveforms has a third amplitude.

Preferably, the entrance and/or exit region comprise a proportion of the total axial length of the first device and/or the second device selected from the group consisting of: (i) <5%; (ii) 5-10%; (iii) 10-15%; (iv) 15-20%; (v) 20-25%; (vi) 25-30%; (vii) 30-35%; (viii) 35-40%; and (ix) 40-45%.

According to an embodiment the first and/or third amplitudes are substantially zero and the second amplitude is substantially non-zero. Preferably, the second amplitude is larger than the first amplitude and/or the second amplitude is larger than the third amplitude.

According to an embodiment one or more transient DC voltages or one or more transient DC voltage waveforms applied to electrodes of the first device and/or the second device pass in use along the first device and/or the second device with a first velocity. Preferably, the first velocity: (i) remains substantially constant; (ii) varies; (iii) increases; (iv) increases then decreases; (v) decreases; (vi) decreases then increases; (vii) reduces to substantially zero; (viii) reverses direction; or (ix) reduces to substantially zero and then reverses direction.

According to an embodiment the one or more transient DC voltages or the one or more transient DC voltage waveforms causes some ions within the first device and/or the second device to pass along the first device and/or the second device with a second different velocity. Preferably, the one or more transient DC voltages or the one or more transient DC voltage waveforms causes some ions within the first device and/or the second device to pass along the first device and/or the second device with a third different velocity. Preferably, the one or more transient DC voltages or the one or more transient DC voltage waveforms causes some ions within the first device and/or the second device to pass along the first device and/or the second device with a fourth different velocity.

According to an embodiment the one or more transient DC voltages or the one or more transient DC voltage waveforms causes some ions within the first device and/or the second device to pass along the first device and/or the second device with a fifth different velocity. Preferably, the difference between the first velocity and the second and/or the third and/or the fourth and/or the fifth velocities is selected from the group consisting of: (i) less than or equal to 50 m/s; (ii) less than or equal to 40 m/s; (iii) less than or equal to 30 m/s; (iv) less than or equal to 20 m/s; (v) less than or equal to 10 m/s; (vi) less than or equal to 5 m/s; and (vii) less than or equal to 1 m/s.

Preferably, the first velocity is selected from the group consisting of: (i) 10-250 m/s; (ii) 250-500 m/s; (iii) 500-750 m/s; (iv) 750-1000 m/s; (v) 1000-1250 m/s; (vi) 1250-1500 m/s; (vii) 1500-1750 m/s; (viii) 1750-2000 m/s; (ix) 2000-2250 m/s; (x) 2250-2500 m/s; (xi) 2500-2750 m/s; and (xii) 2750-3000 m/s. Preferably, the second and/or the third and/or the fourth and/or the fifth velocity is selected from the group consisting of: (i) 10-250 m/s; (ii) 250-500 m/s; (iii) 500-750 m/s; (iv) 750-1000 m/s; (v) 1000-1250 m/s; (vi) 1250-1500 m/s; (vii) 1500-1750 m/s; (viii) 1750-2000 m/s; (ix) 2000-2250 m/s; (x) 2250-2500 m/s; (xi) 2500-2750 m/s; and (xii) 2750-3000 m/s.

According to an embodiment one or more transient DC voltages or one or more transient DC voltage waveforms are applied to electrodes of the first device and/or the second device and have a frequency, and wherein the frequency: (i) remains substantially constant; (ii) varies; (iii) increases; (iv) increases then decreases; (v) decreases; or (vi) decreases then increases.

According to an embodiment one or more transient DC voltages or one or more transient DC voltage waveforms are applied to electrodes of first device and/or the second device and have a wavelength, and wherein the wavelength: (i) remains substantially constant; (ii) varies; (iii) increases; (iv) increases then decreases; (v) decreases; or (vi) decreases then increases.

According to an embodiment two or more transient DC voltages or two or more transient DC voltage waveforms are applied to the first device and/or the second device and pass simultaneously along the first device and/or the second device. According to an embodiment the two or more transient DC voltages or the two or more transient DC voltage waveforms are arranged to move: (i) in the same direction; (ii) in opposite directions; (iii) towards each other; or (iv) away from each other.

Preferably, one or more transient DC voltages or one or more transient DC voltage waveforms pass along the first device and/or the second device and at least one substantially stationary transient DC potential voltage or voltage waveform is provided at a position along the first device and/or the second device.

Preferably, one or more transient DC voltages or one or more transient DC voltage waveforms are repeatedly generated and passed in use along the first device and/or the second device, and wherein the frequency of generating the one or more transient DC voltages or the one or more transient DC voltage waveforms: (i) remains substantially constant; (ii) varies; (iii) increases; (iv) increases then decreases; (v) decreases; or (vi) decreases then increases.

According to an embodiment in use a continuous beam of ions is received at an entrance to the first device and/or the second device. Alternatively, according to an embodiment in use packets of ions are received at an entrance to the first device and/or the second device. Preferably, pulses of ions emerge from an exit of the first device and/or the second device.

According to an embodiment the apparatus further comprises an ion detector, the ion detector being arranged to be substantially phase locked in use with the pulses of ions emerging from the exit of the first device and/or the second device.

According to an embodiment the apparatus further comprises a Time of Flight mass analyser comprising an electrode for injecting ions into a drift region, the electrode being arranged to be energised in use in a substantially synchronised manner with the pulses of ions emerging from the exit of the first device and/or the second device.

Preferably, the first device and/or the second device comprise a plurality of electrodes and wherein at least 10%, 20%, 30%, 40%, 50%, 60%, 70%, 80%, 90%, or 95% of the electrodes are connected to both a DC and an AC or RF voltage supply. According to an embodiment the first device and/or the second device comprise a plurality of electrodes and wherein axially adjacent electrodes are supplied with AC or RF voltages having a phase difference of 180°.

According to an embodiment the second device is arranged to operated at a pressure selected from the group consisting of: (i) <0.0001 mbar; (ii) 0.0001-0.0005 mbar; (iii) 0.0005-0.001 mbar; (iv) 0.001-0.005 mbar; (v) 0.005-0.01 mbar; (vi) 0.01-0.05 mbar; (vii) 0.05-0.1 mbar; (viii) 0.1-0.5 mbar; (ix) 0.5-1 mbar; (x) 1-5 mbar; (xi) 5-10 mbar; (xii) 10-50 mbar; (xiii) 50-100 mbar; (xiv) 100-500 mbar; (xv) 500-1000 mbar; and (xvi) >1000 mbar.

According to an embodiment the second device comprises means for providing a source of gas, wherein in use the gas flows against the direction of travel of ions through the second device.

According to a less preferred embodiment the first device is arranged to separate ions according to their ion mobility i.e. may comprise an ion mobility separator or spectrometer incorporating all the aspects as described above and below with reference to the preferred embodiment. Similarly, according to the less preferred embodiment the second device may be arranged to separate ions according to their rate of change of ion mobility with electric field strength i.e. may comprise a FAIMS device. Again, according to the less preferred embodiment the second device may incorporate all the aspects as described above and below with reference to the preferred embodiment.

The second device preferably comprises a drift tube or region for separating ions according to their ion mobility and wherein the second device further comprises an ion detector arranged at the exit of the drift tube or region for detecting ions which have been transmitted through the drift tube or region.

According to an embodiment the second device comprises a gate electrode or mesh electrode arranged at an upstream region of the drift tube or region and wherein a voltage is periodically applied to the gate electrode or mesh electrode in order to pulse ions into the drift tube or region. The second device may comprise an electrode or mesh electrode arranged at a downstream region of the drift tube or region in order to shield the ion detector.

According to an embodiment the second device comprises a drift tube or region for separating ions according to their ion mobility and wherein the second device further comprises an orthogonal acceleration electrode for orthogonally accelerating ions into the drift tube or region. The second device may comprise a trapping region for trapping ions and a drift region in which ions are separated according to their ion mobility. The trapping region may comprise at least one electrode or mesh electrode for axially confining ions within the trapping region and wherein ions are, in use, periodically released or pulsed out of the trapping region into the drift region. Ions are preferably accumulated in use within the trapping region whilst other ions are being separated according to their ion mobility in the drift region.

The apparatus preferably further comprises a continuous or pulsed ion source. According to an embodiment an ion source may be provided selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source.

The apparatus may further comprise a separation device for separating a sample to be analysed prior to ionisation. The separation device is preferably selected from the group consisting of: (i) a liquid chromatography device; (ii) a gas chromatography device; (iii) a super-critical fluid chromatography device; (iv) a capillary electrophoresis device; and (v) a capillary electrophoresis chromatography device.

According to an aspect of the present invention there is provided a mass spectrometer comprising the apparatus as described above. Preferably, the second device is arranged in a first vacuum chamber of the mass spectrometer. According to an embodiment the mass spectrometer further comprises a second vacuum chamber downstream of the second device.

Preferably, one or more AC or RF ion guides are arranged in the first and/or second vacuum chambers. According to an embodiment the mass spectrometer further comprises a further vacuum chamber arranged upstream of the first vacuum chamber.

According to an embodiment the mass spectrometer further comprises a mass analyser. Preferably, the mass analyser is selected from the group consisting of: (i) an orthogonal acceleration Time of Flight mass analyser; (ii) an axial acceleration Time of Flight mass analyser; (iii) a Paul 3D quadrupole ion trap mass analyser; (iv) a 2D or linear quadrupole ion trap mass analyser; (v) a Fourier Transform Ion Cyclotron Resonance mass analyser; (vi) a magnetic sector mass analyser; (vii) a quadrupole mass analyser; and (viii) a Penning trap mass analyser.

According to an embodiment the mass spectrometer further comprises a collision or fragmentation cell. The collision or fragmentation cell preferably comprises AC or RF means for generating an AC or RF electric field for radially confining ions within the collision or fragmentation cell. Preferably, the collision or fragmentation cell comprises means for generating a constant DC electric field across at least 10%, 20%, 30%, 40%, 50%, 60%, 70%, 80%, 90% or 95% of the axial length of the collision or fragmentation cell. Preferably, there is also provided means for generating a transient or time varying DC voltage or potential waveform for urging ions along and through the collision or fragmentation cell. The collision or fragmentation cell may comprise a surface for surface induced decomposition.

According to another aspect of the present invention there is provided a method of separating ions comprising:

separating ions according to their ion mobility or according to their rate of change of ion mobility with electric field strength in a first device; and then separating ions according to their ion mobility or according to their rate of change of ion mobility with electric field strength in a second device, the second device being arranged downstream of the first device.

According to a further aspect of the present invention there is provided a method of mass spectrometry comprising the method of separating ions as described above.

The preferred embodiment relates to apparatus comprising a Field Asymmetric Ion Mobility Spectrometry device coupled in series with an ion mobility separator or spectrometer.

A sample to be analysed is preferably first ionised in an ion source. The ions are then preferably passed into a first device which preferably comprises a Field Asymmetric Ion Mobility Spectrometry ("FAIMS") device wherein the ions are preferably separated according to the rate of change of their ion mobility with electric field strength. Ions having similar ion mobility dependence upon electric field strength preferably emerge from the FAIMS device and are then preferably passed or transmitted to a second device which preferably comprises an ion mobility separator or spectrometer for separating ions according to their ion mobility. The ion mobility separator or spectrometer preferably comprises a drift tube. The ions are then preferably separated according to their ion mobility in the ion mobility separator or spectrometer. At least some of these ions are then preferably detected by an ion detector.

The mobility of an ion is generally inversely proportional to its cross sectional area and proportional to its charge. The drift time of an ion through the drift tube of an ion mobility separator or spectrometer is therefore preferably approximately proportional to the length of the drift tube and inversely proportional to the ion mobility and the electric field strength maintained along the length of the drift tube. Hence, to a first approximation, the drift time of an ion through an ion mobility separator or spectrometer is proportional to the cross sectional area of the ion.

On the other hand the rate of change of ion mobility with electric field strength in a FAIMS device is generally unpredictable. It is not believed to be directly proportional to the ion mobility, nor to the ion cross sectional area, nor to the charge of the ion.

Accordingly, the parameters that determine the separation of ions in an ion mobility separator or spectrometer are quite different to the parameters that determine the separation of ions in a Field Asymmetric Ion Mobility Spectrometry device. According to a preferred embodiment therefore ions can be separated differently by passing ions first through a FAIMS device and then through an ion mobility separator or spectrometer. Accordingly, at least to some degree, the ion separating properties of the FAIMS device are different to and complementary to the ion separating properties of ion mobility separator or spectrometer. The combination of a FAIMS device in series with an ion mobility separator or spectrometer provides a greater or higher overall ion separating capability, or specificity. Ions can therefore separated to a much greater resolution according to the preferred embodiment.

In the preferred embodiment the ions preferably first pass through a Field Asymmetric Ion Mobility Spectrometry device. Ions which emerge from the FAIMS device are then preferably directed or arranged to pass through an ion mobility separator or spectrometer which preferably comprises a drift tube. The ion mobility separator or spectrometer preferably separates and preferably detects all the ions onwardly transmitted from the Field Asymmetric Ion Mobility Spectrometry device.

The Field Asymmetric Ion Mobility Spectrometry device may be switched to different settings or may be scanned through or between a range of different settings. In this way a two dimensional separation of ions emerging from the ion source may be effected. In effect it can be considered that in one axis or dimension ions are separated according to their ion mobility whilst in the other axis or dimension ions are separated according to their rate of change of ion mobility with electric field strength.

In a particular embodiment of the present invention the drift tube of the ion mobility separator or spectrometer may be maintained at sub-atmospheric pressure. The ion mobility separator or spectrometer preferably comprises a plurality of electrodes and an AC or RF voltage is preferably applied to at least some of the electrodes in order to generate an AC or RF electric field which acts to radially confine ions near to a central axis of the device. The AC or RF electric field may be applied to or maintained between neighbouring rods in a segmented multipole rod set, or between neighbouring rings in a ring stack. The drift tube is preferably maintained at a pressure between 1000 mbar and $10^{-4}$ mbar, further preferably between 100 mbar and $10^{-3}$ mbar, further preferably between 10 mbar and $10^{-2}$ mbar, further preferably between 1 mbar and $10^{-1}$ mbar.

In an embodiment the ion mobility separator or spectrometer may be maintained at sub-atmospheric pressure and an AC or RF electric field may be used to radially confine the ions near to a central axis of the device. However, instead of an axial DC voltage gradient being maintained along the length of the ion mobility separator or spectrometer a DC travelling voltage wave or a time varying or transient DC potential voltage or potential waveform may be applied to the electrodes in order to propel ions through the drift tube of the ion mobility separator or spectrometer. The travelling wave amplitude and the velocity of the transient voltage waveform may be adjusted such that some ions effectively are not trapped by the applied DC voltages but instead are nudged towards the exit of the device and experience the effects of the successive DC voltages being applied to the device. Ions with a higher mobility will slip less readily than those ions with a lower mobility. As a consequence, ions with a higher ion mobility will tend to be urged towards the end of the drift tube of the ion mobility separator or spectrometer more quickly than ions having a relatively lower ion mobility. This method can therefore be used to separate ions according to their mobility.

According to an alternative and less preferred embodiment the ions may initially pass through an ion mobility separator comprising a drift tube and then pass through a Field Asymmetric Ion Mobility Spectrometry device arranged downstream of the ion mobility separator. Ions transmitted through the Field Asymmetric Ion Mobility Spectrometry device may be detected by a detector positioned at the exit of the Field Asymmetric Ion Mobility Spectrometry device. The same ion separation may accordingly be effected, but in the reverse sequence or manner to the preferred embodiment i.e. it is preferred that the ion mobility separator is arranged downstream of the FAIMS device, but less preferably the ion mobility separator may be arranged upstream of the FAIMS device.

According to an embodiment the ions emerging from the combination of a FAIMS device and an ion mobility separator may then be passed into the main housing or body of a mass spectrometer for further analysis. In the mass spectrometer the ions are preferably further separated according to their mass to charge ratio and then detected. This provides even greater specificity. Accordingly, specific ions can be detected and quantified with a high degree of confidence even when the original material to be analysed comprising a complex mixture. It also allows specific ions to be isolated from a complex mixture and identified by accurate determination of their mass to charge ratio.

In an embodiment the mass spectrometer may comprise a tandem mass spectrometer wherein ions are mass filtered and specific ions are transmitted and then fragmented in an ion fragmentation device or collision cell. The resulting product, daughter or fragment ions may then preferably be mass analysed. This provides even greater specificity and again allows specific ions to be detected and quantified with a very high degree of confidence, even if the original material to be analysed is a very complex mixture. Specific ions can also be isolated from a very complex mixture and identified from the determination of the mass to charge ratios of their corresponding fragment ions.

The mass spectrometer may comprise a quadrupole mass filter, a 3D quadrupole ion trap, a linear quadrupole ion trap, a Time of Flight mass spectrometer, an orthogonal acceleration Time of Flight mass spectrometer, a magnetic sector mass spectrometer or a Fourier Transform Ion Cyclotron Resonance mass spectrometer. The tandem mass spectrometer may comprise any combination of the above.

The fragmentation means or fragmentation cell preferably comprises a gas collision cell. The gas collision cell may use an AC or RF electric field to radially confine ions and an axial DC electric field and/or a travelling or transient DC voltage wave to urge ions through the gas collision cell. The collision cell may comprise means for trapping ions or a surface for surface induced decomposition.

The ionisation source may comprise a gaseous phase ionisation source including a radiation ionisation source, an Electrospray Ionisation ion source (ESI), an Atmospheric Pressure Chemical Ionisation ion source (APCI), an Atmospheric Pressure Photoionisation ion source (APPI), an Atmospheric Pressure Laser Desorption/Ionisation ion source (AP-LDI), an Atmospheric Pressure Matrix Assisted Laser Desorption/Ionisation ion source (AP-MALDI), or an Atmospheric Pressure Desorption/Ionisation On Silicon ion source (AP-DIOS).

In a further embodiment the sample to be analysed may be first separated by chromatography before being transported to the ion source for ionisation. The means for chromatographic separation may comprise gas chromatography, super-critical fluid chromatography, liquid chromatography, capillary electrophoresis or capillary electrophoresis chromatography.

BRIEF DESCRIPTION OF THE DRAWINGS

Various embodiments of the present invention will now be described together with other arrangements given for illustrative purposes only, by way of example only, and with reference to the accompanying drawings in which.

DETAILED DESCRIPTION OF THE PREFERRED EMBODIMENTS

Figure 1:
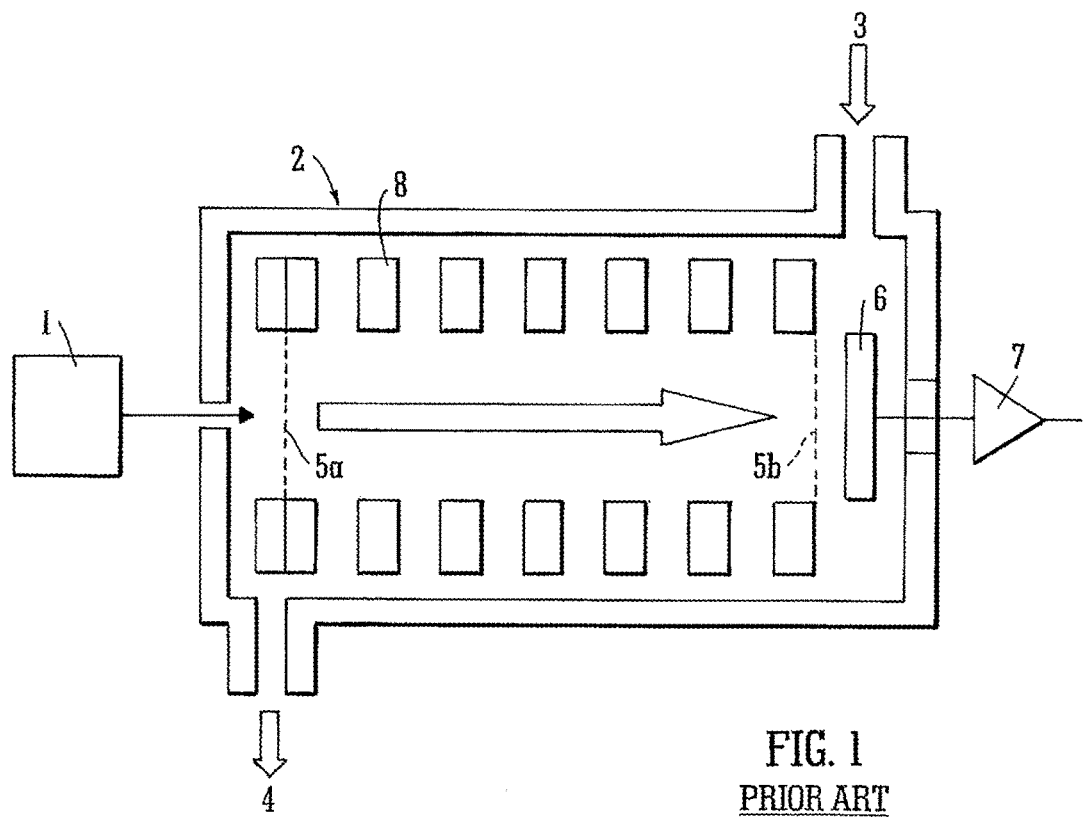
FIG. 1 shows a known ion mobility spectrometer.

FIG. 1 shows the configuration of a known ion mobility spectrometer. Ions are produced or generated in an ion source 1 and are then directed into an ion mobility spectrometer 2 which comprises a drift tube. The drift tube comprises a plurality of annular electrodes 8 which are arranged along the length of the drift tube. A constant DC voltage is maintained along the length of the drift tube in order to force or propel ions along and through the drift tube. Ions entering the ion mobility spectrometer 2 are initially prevented from passing into or further along the drift tube by the application of a voltage or gating potential to a first mesh electrode 5a arranged at the entrance to the ion mobility spectrometer 2.

The first mesh electrode 5a, which functions as an ion gate, is periodically pulsed to a relatively low voltage thereby allowing a packet ions to pass through the first mesh electrode 5a and enter the drift tube and hence the main body of the ion mobility spectrometer 2.

A packet of ions entering the drift tube 2 will experience a constant axial DC electric field which is maintained along or across the electrodes 8. Under the action of the resulting axial electric field ions are caused to drift towards the exit end of the drift tube 2 against a counter current or counter flow of gas. The counter current or counter flow of gas is maintained by introducing a stream of gas 3 via a port arranged towards the exit of the drift tube 2. The gas flows out of the port and towards the entrance region of the ion mobility spectrometer 2 against the direction of travel of ions passing through the ion mobility spectrometer 2. The gas then exits the drift tube 2 via a further port adjacent to the entrance region of the ion mobility spectrometer 2 and exits 4 the chamber housing the ion mobility spectrometer 2.

Ions as they arrive at the exit of the drift tube or ion mobility spectrometer 2 are arranged to impinge upon a plate or ion detector 6. The ion detector 6 is electrically shielded from the drift tube 2 and vice versa by a second mesh electrode 5b. The output ion current from the ion detector 6 is amplified by an amplifier 7.

The ion mobility spectrometer 2 shown in FIG. 1 is effective in separating ions according to their ion mobility and detecting the ions. Ions with the smallest cross section and therefore highest mobility will tend to be the first ions which travel to the exit end of the ion mobility spectrometer 2 and hence be detected by the ion detector 6.

Figure 2:
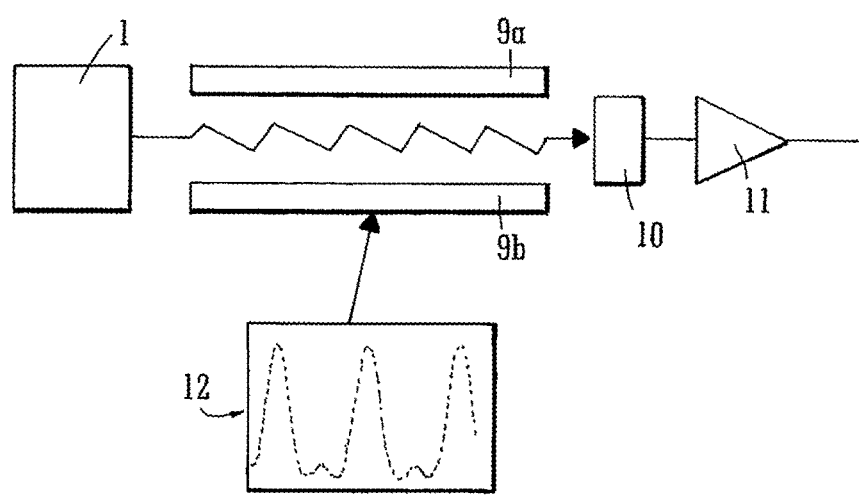
FIG. 2 shows a known Field Asymmetric Ion Mobility Spectrometry device.

FIG. 2 shows a known Field Asymmetric Ion Mobility Spectrometry ("FAIMS") spectrometer. Ions are produced or generated in an ion source 1 and are then directed to pass between two parallel metal electrodes 9a,9b. A flow of gas may be used to direct or guide ions from the ion source 1 into and through the gap between the two electrodes 9a,9b.

An asymmetric periodic voltage waveform 12 and a DC compensation voltage are applied to the two parallel metal electrodes 9a,9b. Ions possessing an ion mobility that changes in a specific way as a function of electric field strength varies will be transmitted between the two electrodes 9a,9b whereas all other ions will tend to migrate towards one of the two electrode 9a,9b. Those ions which migrate towards one of the two electrodes 9a,9b will become discarded or otherwise lost to the system.

Those ions that are onwardly transmitted by the FAIMS device or FAIMS spectrometer are then detected by a plate or ion detector 10 arranged at the exit of the FAIMS device. The ion current output from the ion detector 10 is amplified by an amplifier 11.

Figure 3:
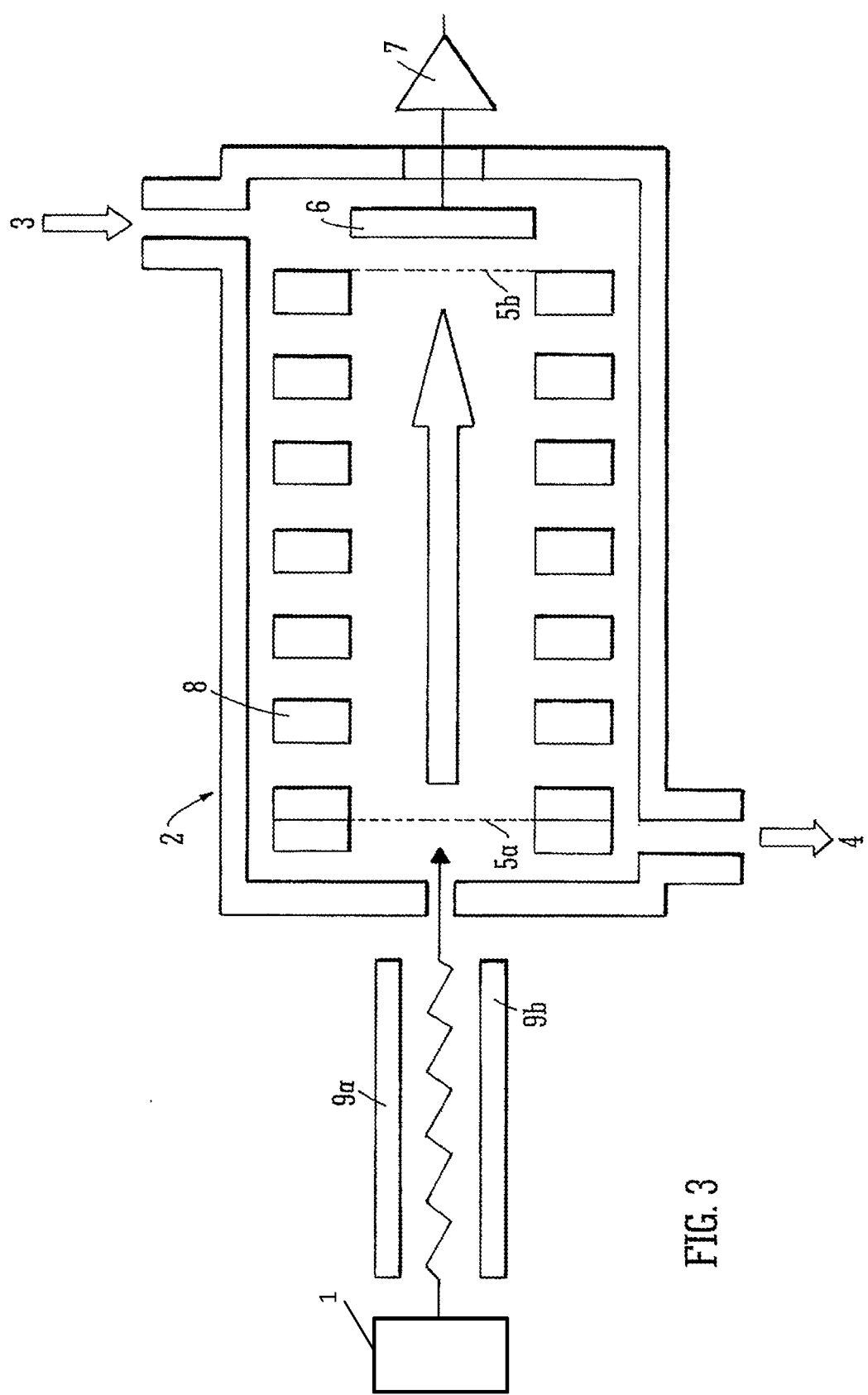
FIG. 3 shows a first embodiment of the present invention wherein a FAIMS device is provided in series with an ion mobility spectrometer wherein ions are axially accelerated through the ion mobility spectrometer.

FIG. 3 shows a first embodiment of the present invention and shows a FAIMS device coupled to an ion mobility spectrometer 2. Ions are produced or generated in an ion source 1 and are then preferably directed to or otherwise transmitted to a Field Asymmetric Ion Mobility Spectrometry ("FAIMS") device. The FAIMS device preferably comprises two parallel metal electrodes 9a,9b. However, according to alternative embodiments the FAIMS device may comprise two concentric cylindrical electrodes or other arrangements.

A flow of gas is preferably used to direct the ions from the ion source into and through the gap between the two electrodes 9a,9b. An asymmetric periodic waveform and a DC compensation voltage are preferably applied to the two electrodes 9a,9b. Ions with an ion mobility that changes in a specific way as a function of electric field strength or as the electric field strength is varied are preferably onwardly transmitted between the electrodes 9a,9b and emerge from the exit of the FAIMS device. All other ions will tend to migrate towards one of the two electrodes 9a,9b and hence will become discarded or otherwise lost to the system. Those ions that are transmitted through the FAIMS device are then preferably directed into an ion mobility spectrometer 2 which is preferably arranged axially and which is preferably downstream of the FAIMS device.

The ion mobility spectrometer 2 preferably comprises a drift tube comprising a plurality of annular electrodes 8. However, according to other embodiments the electrodes may comprise rod electrodes or wire loops.

A first mesh electrode 5a is preferably arranged at the entrance to the ion mobility spectrometer 2. The first mesh electrode 5a preferably acts as a gate electrode and when an appropriate gating voltage is applied to the first mesh electrode ions are prevented from passing any further along or into the ion mobility spectrometer 2. The first mesh electrode 5a is therefore preferably used as an ion gate and is preferably periodically pulsed to a relatively low voltage to allow ions to pass.

A constant DC voltage gradient is preferably maintained along the length of the ion mobility spectrometer 2. Under the action of the constant axial DC electric field a packet of ions which is pulsed into the ion mobility spectrometer 2 is preferably arranged to drift to the exit end of the drift tube or ion mobility spectrometer 2 preferably against a counter current or counter flow of gas.

The counter current or counter flow of gas is preferably achieved by introducing a stream of gas 3 via a port located adjacent to an exit region of the drift tube or ion mobility spectrometer 2. The gas preferably flows towards the entrance of the drift tube or ion mobility spectrometer 2 against the direction of travel of ions through the ion mobility spectrometer 2 before exiting the drift tube or ion mobility spectrometer 2 via a port adjacent to an entrance region of the drift tube or ion mobility spectrometer 2.

Ions arriving at the exit of the drift tube or ion mobility spectrometer 2 are preferably detected on a plate or ion detector 6. The ion detector 6 is preferably shielded from the drift tube 2 and vice versa by a second mesh electrode 5b. The ion current output from the detector 6 is preferably amplified by an amplifier 7.

The combination of a FAIMS device and an ion mobility separator or spectrometer as shown in FIG. 3 preferably enables ions to be separated and preferably detected according to their ion mobility with a much greater resolution than conventional arrangements.

Figure 4:
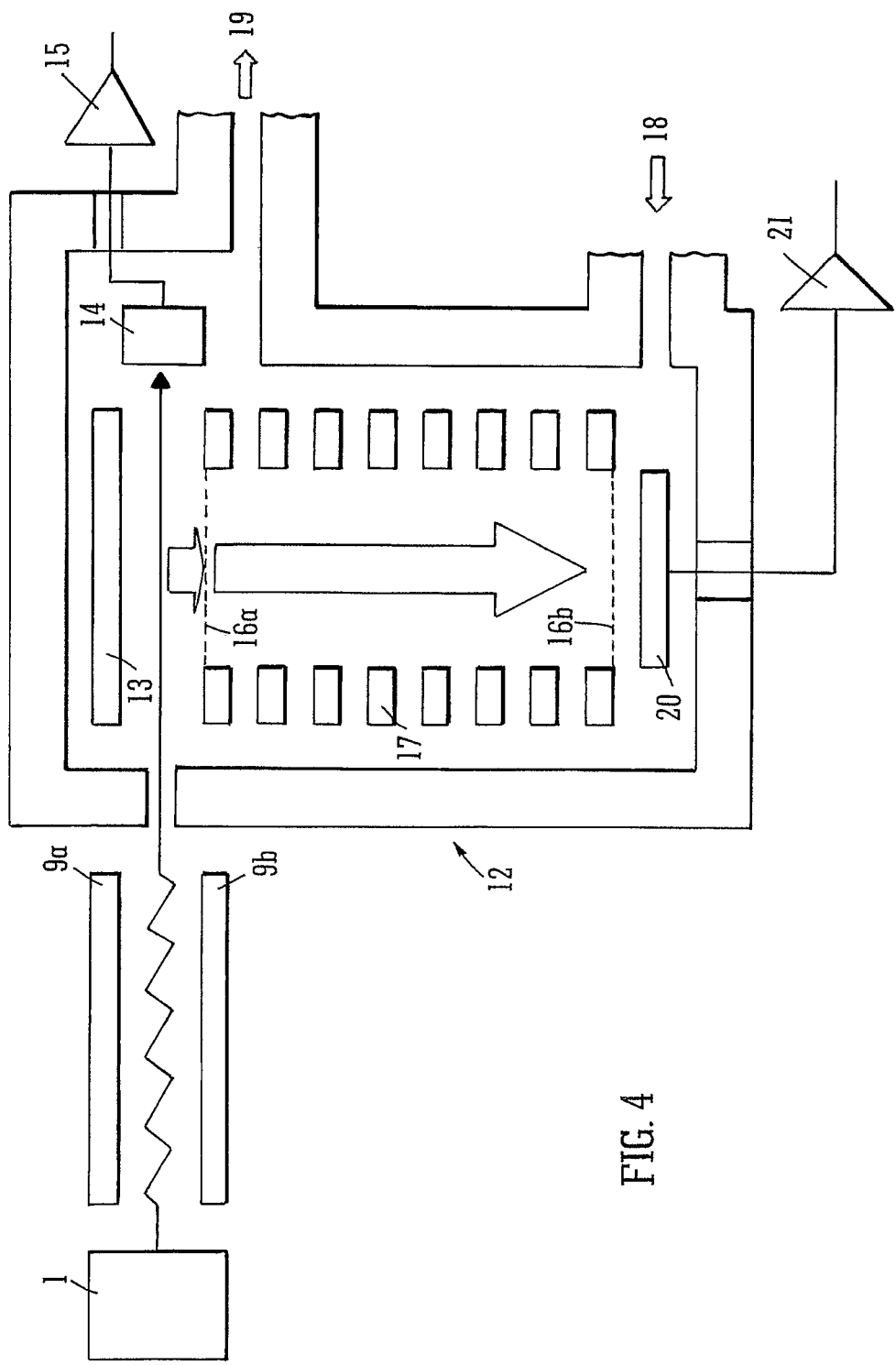
FIG. 4 shows a second embodiment of the present invention wherein a FAIMS device is provided in series with an ion mobility spectrometer wherein ions are orthogonally accelerated through the ion mobility spectrometer.

FIG. 4 shows a second embodiment of the present invention. Many aspects of this embodiment are similar to the first embodiment described above with reference to FIG. 3. According to this embodiment ions are preferably produced or generated in an ion source 1 and are then preferably directed to or transmitted to a Field Asymmetric Ion Mobility Spectrometry ("FAIMS") device. The FAIMS device preferably comprises two parallel metal electrodes 9a,9b although according to alternative embodiments the FAIMS device may comprise two concentric cylindrical electrodes or other electrode arrangements. A flow of gas is preferably used to direct the ions into and through the gap between the two electrodes 9a,9b. An asymmetric periodic waveform and a DC compensation voltage are preferably applied to the two electrodes 9a,9b. Ions with an ion mobility that changes in a specific way as the electric field strength is changed are preferably onwardly transmitted between the electrodes 9a,9b and preferably emerge from the exit of the FAIMS device. All other ions will tend to migrate to one of the two electrodes 9a,9b and hence will preferably be discarded or otherwise lost to the system.

The ions that are onwardly transmitted through the FAIMS device are preferably directed into an ion mobility spectrometer 12. The ion mobility spectrometer 12 preferably comprises a drift tube which is preferably arranged orthogonally to the initial direction of travel of ions into the ion mobility spectrometer 12. Ions received by the ion mobility spectrometer 12 may pass on to a first plate or ion detector 14 which is preferably arranged opposed to the entrance aperture of the ion mobility spectrometer 12. The ion current output from the ion detector 14 is preferably amplified by a first amplifier 15.

In a mode of operation a voltage is preferably periodically applied to an orthogonal acceleration electrode 13 which is preferably arranged in the entrance region of the ion mobility spectrometer 12. An electric field is preferably generated between the orthogonal acceleration electrode 13 and a first mesh electrode 16a which is preferably arranged at the entrance to the drift tube which forms part of the ion mobility spectrometer 12. The orthogonal electric field preferably causes a packet of ions in the entrance region of the ion mobility spectrometer 12 to be orthogonally accelerated into the main portion of the ion mobility spectrometer 12 which preferably comprises a drift tube or drift region.

The ions which are orthogonally accelerated preferably pass through the first mesh electrode 16a such that a packet of ions then preferably enters a drift tube which is preferably arranged orthogonally to the initial direction of ions entering the ion mobility spectrometer 12.

An axial DC electric field is preferably maintained along the length of the drift tube or ion mobility spectrometer 12. Under the action of the axial DC electric field, ions are preferably caused to drift to the exit end of the drift tube or ion mobility spectrometer 12 preferably against a counter current or counter flow of gas.

The counter current or counter flow of gas is preferably achieved by introducing a stream of gas 18 via a port adjacent to the exit region of the drift tube or ion mobility spectrometer 12. The gas preferably flows towards an entrance region of the drift tube or ion mobility spectrometer 12 before preferably exiting the drift tube or ion mobility spectrometer 12 via a port located in the vicinity of the first ion detector 14.

Ions arriving at the exit of the drift tube or ion mobility spectrometer 12 are preferably detected on a second plate or ion detector 20 and the ion current output from the second plate or ion detector 20 is preferably amplified by a second amplifier 21.

According to the embodiment shown and described with reference to FIG. 4 ions are first separated in a Field Asymmetric Ion Mobility Spectrometer device according to their ion mobility as a function of electric field strength and are then preferably separated and detected according to their ion mobility.

Figure 5:
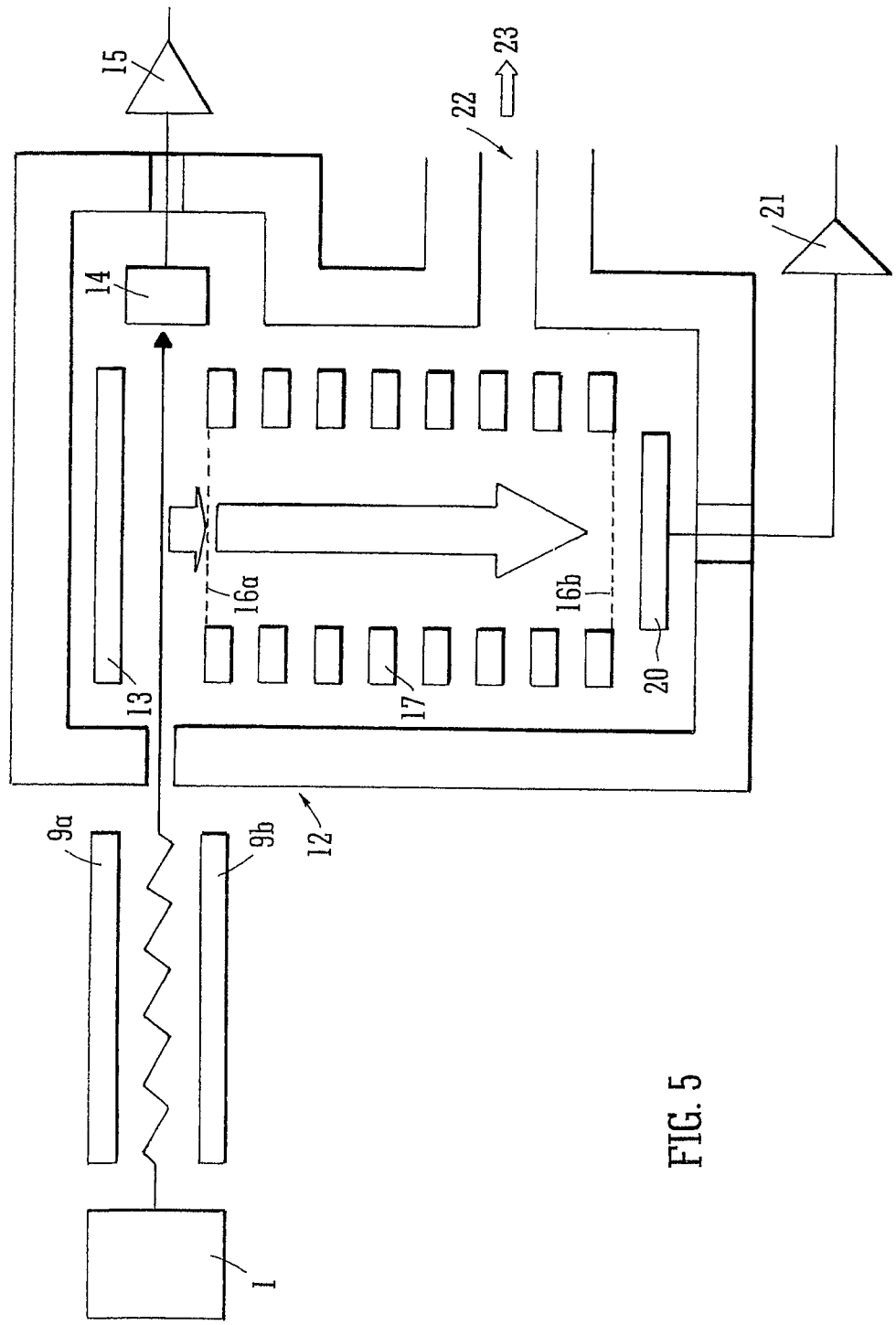
FIG. 5 shows a third embodiment of the present invention wherein a FAIMS device is provided in series with an ion mobility spectrometer which is maintained at a relatively low pressure within a vacuum chamber.

FIG. 5 shows a third embodiment of the present invention which is similar in many respects to the embodiment shown and described above with respect to FIG. 4 except that the drift tube or ion mobility spectrometer 12 is preferably maintained under or at a partial vacuum i.e. the ions do not prefer move against a counter flow of gas.

Ions are preferably produced or generated in an ion source 1 and are then preferably directed to or transmitted to a Field Asymmetric Ion Mobility Spectrometry or FAIMS device. The FAIMS device preferably comprises two parallel metal electrodes 9a,9b although according to an alternative embodiment the FAIMS device may comprise two concentric cylindrical electrodes or alternative arrangements of electrodes. A flow of gas is preferably used to direct the ions into and through the gap between the two electrodes 9a,9b forming the FAIMS device. An asymmetric periodic waveform and a DC compensation voltage are preferably applied to the two electrodes 9a,9b. Ions with an ion mobility that changes in a specific way as the electric field strength is changed are preferably transmitted between the electrodes 9a,9b and preferably emerge from the exit of the FAIMS device. All other ions will tend to migrate to one of the two electrodes 9a,9b and hence will tend to be discarded or otherwise lost to the system.

The ions that are transmitted through the FAIMS device are preferably directed into a drift tube of the ion mobility spectrometer 12.

The drift tube of the ion mobility spectrometer 12 is preferably contained within a vacuum chamber that is preferably maintained under or at a partial vacuum at a pressure preferably of 0.1-1 mbar by a vacuum pump that preferably removes gas 23 via a pumping port 22. Ions transmitted by the FAIMS device are preferably drawn into the vacuum chamber. In a mode of operation the ions may then pass to a first plate or ion detector 14 whereupon they are detected.

The ion current output from the first plate or ion detector 14 is then preferably amplified by a first amplifier 15.

In another mode of operation a voltage is preferably periodically applied to an orthogonal acceleration electrode 13 arranged between the entrance of the ion mobility spectrometer 12 and the first ion detector 14. Ions which enter the ion mobility spectrometer 12 are preferably orthogonally accelerated by an electric field maintained between the orthogonal acceleration electrode 13 and a first mesh electrode 16a which preferably is arranged at the entrance to the drift tube. The voltage applied to the first mesh electrode 16a is preferably periodically lowered and a packet of ions will preferably pass through the first mesh electrode 16a. The packet of ions will then preferably enter a part of the drift tube in which an axial DC electric field is preferably maintained between the annular electrodes 17 which preferably comprise the ion mobility spectrometer 12. According to alternative embodiments the electrodes 17 forming the drift tube or drift region may comprise rod electrodes or wires.

An axial DC electric field is preferably maintained along the length of the ion mobility spectrometer 12 and the electrodes 17 which form the ion mobility spectrometer 12 by applying a series of DC voltages to the stack or series of ring or annular electrodes 17.

In all the embodiments of the present invention including the first and second embodiments shown and described with reference to FIGS. 3 and 4 and also in the third embodiment shown and described with reference to FIG. 5 AC or RF voltages may also preferably be applied between neighbouring rings or annular electrodes 17 (or rod or alternative arrangements of electrodes) in the stack or series of ring, annular or rod electrodes 17 which are preferably arranged along the length of the ion mobility spectrometer 12.

Under the action of the applied AC or RF electric field to the electrodes 17 of the ion mobility spectrometer 12 the ions within the ion mobility spectrometer 12 are preferably confined to a region about the central axis of the stack or series of ring, annular or rod electrodes 17 whilst simultaneously under the action of the applied axial DC electric field the ions are preferably caused to drift towards the exit region of the drift tube or ion mobility spectrometer 12.

The radial confinement of ions due to the AC or RF electric field preferably prevents ions from migrating away from the central axis and becoming lost to the ring or rod electrodes 17 or otherwise to the system. Ions arriving at the exit region of the drift tube or ion mobility spectrometer 12 are preferably detected on a second plate or ion detector 20 and the ion current output from the second plate or ion detector 20 is preferably amplified by a second amplifier 21.

The second ion detector 20 is preferably shielded from the drift tube or ion mobility spectrometer 12 and vice versa by a second mesh electrode 16b.

The combination of a FAIMS device and an ion mobility spectrometer as shown in FIG. 5 preferably enables ions which have first been separated in a Field Asymmetric Ion Mobility Spectrometer device to then preferably be separated and detected according to their ion mobility.

Figure 6:
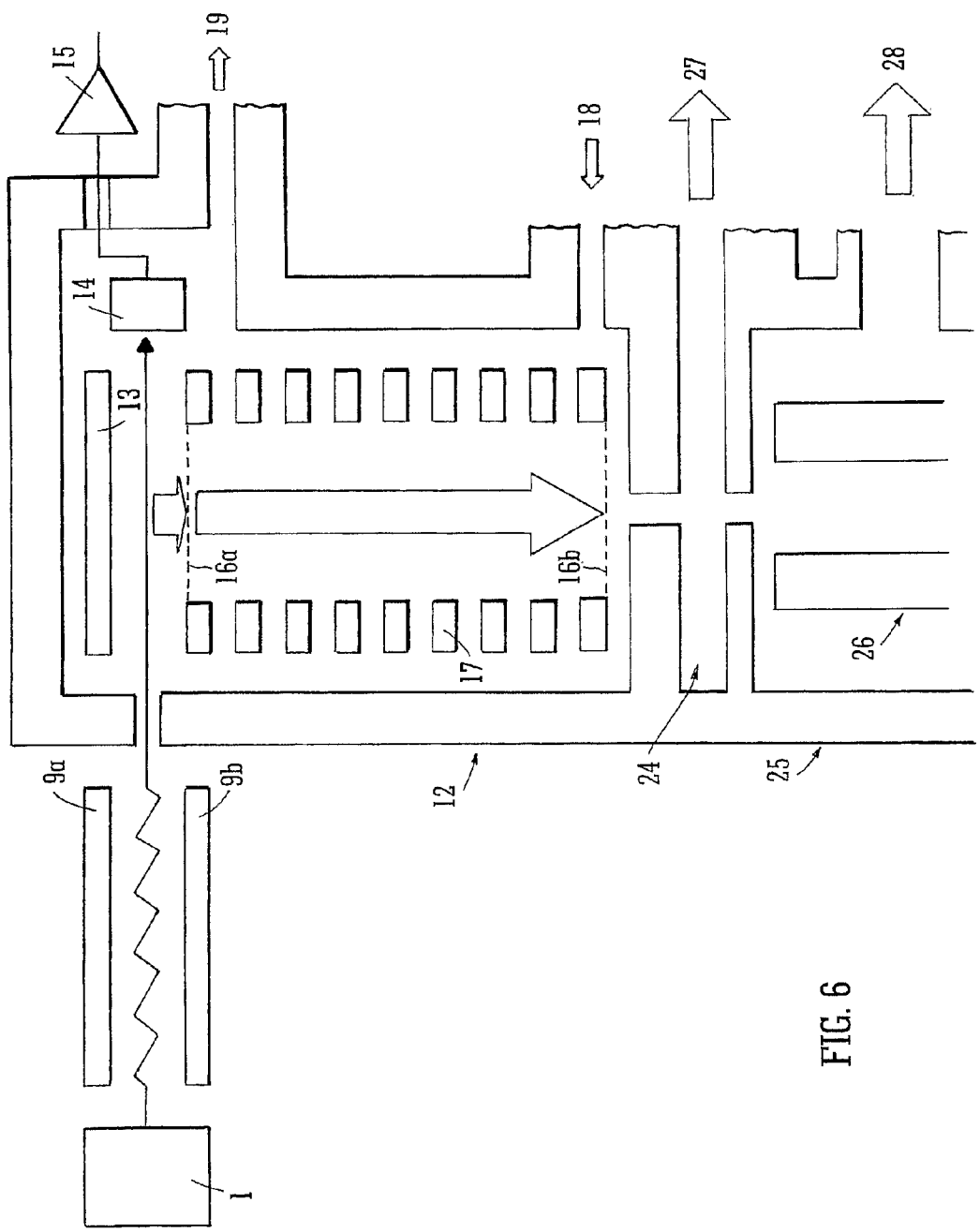
FIG. 6 shows a fourth embodiment of the present invention wherein a FAIMS device is provided in series with an ion mobility separator arranged upstream of the main housing of a mass spectrometer.

FIG. 6 shows a fourth embodiment of the present invention which is similar to the second embodiment shown and described above with reference to FIG. 4. Ions are produced or generated in an ion source 1 and are then preferably directed to or transmitted to a Field Asymmetric Ion Mobility Spectrometry ("FAIMS") device. The FAIMS device preferably comprises two parallel metal electrodes 9a,9b although according to an alternative embodiment the FAIMS device may comprise two concentric cylindrical electrodes or alternative arrangements of electrodes. Ions that are onwardly transmitted by the FAIMS device are preferably directed into an ion mobility separator device and may in a mode of operation pass on to a first plate or ion detector 14. The ion current output from the first plate or ion detector 14 is preferably amplified by an amplifier 15.

In another mode of operation a voltage is preferably periodically applied to an orthogonal acceleration electrode 13 arranged between the entrance of the ion mobility separator 12 and the first ion detector 14. Ions are preferably orthogonally accelerated by an electric field maintained between the orthogonal acceleration electrode 13 and a first mesh electrode 16a which is preferably arranged at the entrance to the drift tube of the ion mobility separator 12. A packet of ions is preferably pulsed into the drift tube of the ion mobility separator and preferably passes through the first mesh electrode 16a.

An axial DC electric field is preferably maintained along the length of the ion mobility spectrometer by applying DC voltages to the electrodes 17 forming the drift tube or ion mobility separator device. Ions preferably drift to the exit end of the drift tube or ion mobility separator preferably against a counter current or counter flow of gas. The counter current or counter flow of gas is preferably achieved by introducing a stream of gas 18 via a port adjacent to the exit region of the drift tube or ion mobility separator 12. The gas flows towards an entrance region of the drift tube or ion mobility separator 12 before exiting the drift tube or ion mobility separator 12 via a port located in the vicinity of the first ion detector 14.

In this embodiment, ions arriving at the exit of the drift tube or ion mobility separator are then preferably drawn into a first vacuum chamber 24 of a mass spectrometer i.e. the ions are preferably not then directly detected by a second ion detector arranged immediately at the exit of the drift tube or ion mobility separator 12 as in the first, second and third embodiments.

The ions then preferably pass from the first vacuum chamber 24 into a second vacuum chamber 25 of the mass spectrometer. An AC or RF ion guide 26 is preferably provided in the second vacuum chamber 25 and preferably acts as an ion guide to guide ions into the main housing of the mass spectrometer.

According to this embodiment, ions having first been separated in a Field Asymmetric Ion Mobility Spectrometry device are then further separated in an ion mobility separator before then subsequently being mass analysed and detected in a mass spectrometer.

Figure 7:
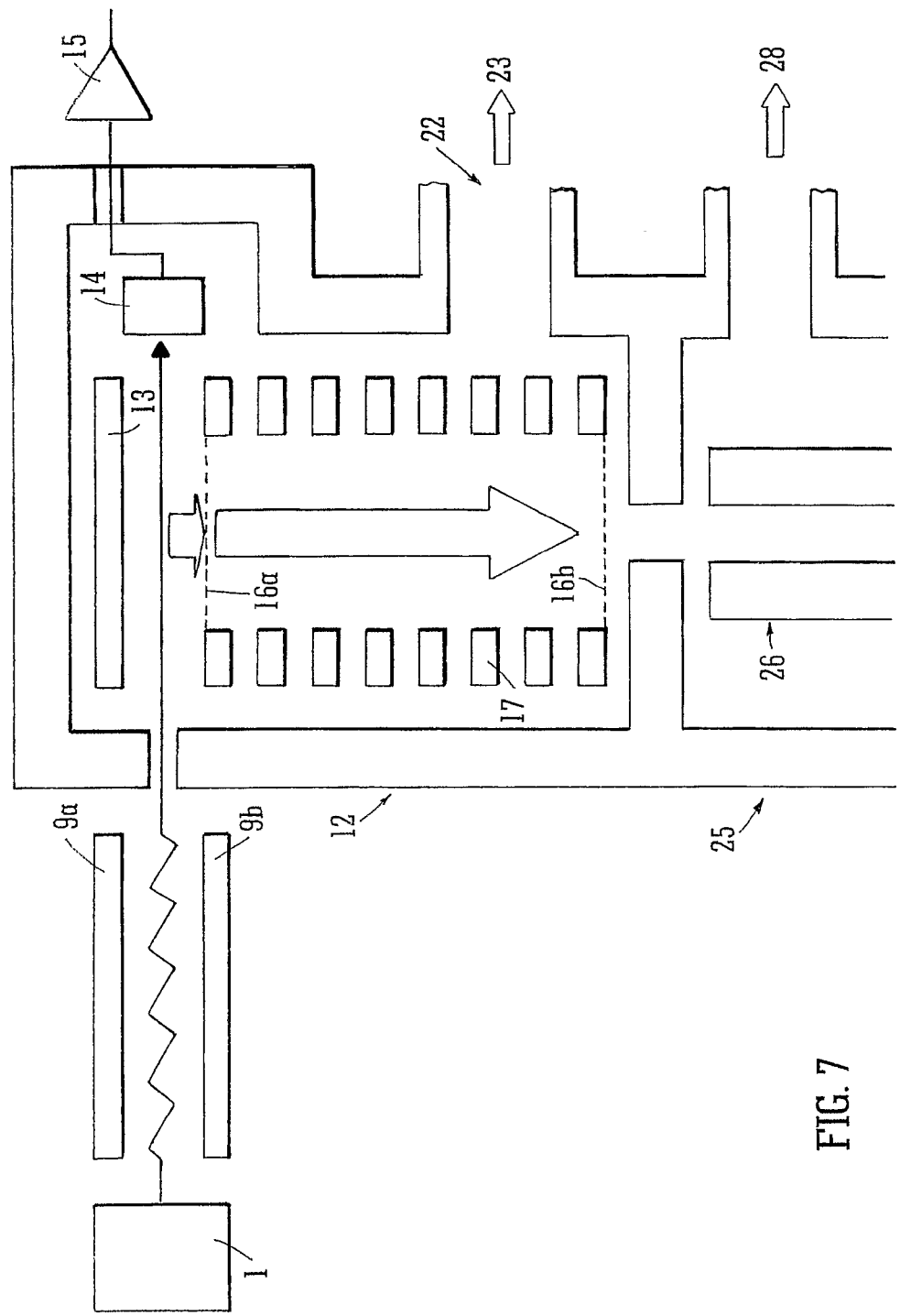
FIG. 7 shows a fifth embodiment of the present invention wherein a FAIMS device is provided in series with an ion mobility separator which forms an initial stage of a mass spectrometer.

FIG. 7 shows a fifth embodiment of the present invention which is similar to the fourth embodiment as described above with reference to FIG. 6 except that the drift tube or ion mobility separator 12 is preferably arranged in a vacuum chamber i.e. ions passing through the drift tube or ion mobility separator preferably do not flow against a counter flow of gas.

Ions are preferably produced or generated in an ion source 1 and are then preferably directed to or transmitted to a Field Asymmetric Ion Mobility Spectrometry ("FAIMS") device. The FAIMS device preferably comprises two parallel metal electrodes 9a,9b although according to an alternative embodiment the FAIMS device may comprise two concentric cylindrical electrodes or alternative electrode arrangements.

Ions that are onwardly transmitted from the FAIMS device are then preferably directed into a mass spectrometer which comprises an ion mobility separator 12 comprising a drift tube as an initial stage.

The drift tube or ion mobility spectrometer 12 is preferably contained within a vacuum chamber which is preferably maintained under a partial vacuum at a pressure of 0.1-1 mbar by a vacuum pump that removes gas 23 via a vacuum port 22. Ions which are drawn into the vacuum chamber may in a mode of operation pass to a plate or ion detector 14 which is preferably arranged opposed to the entrance of the ion mobility separator 12. An ion current output from the plate or ion detector 14 is preferably amplified by an amplifier.

A voltage is preferably periodically applied to an orthogonal acceleration electrode 13 which is preferably arranged between the entrance region of the ion mobility separator 12 and the ion detector 14. Ions are preferably periodically orthogonally accelerated through a first mesh electrode 16a into the main body of the drift tube or ion mobility separator in a similar manner to previously described embodiments.

An axial DC electric field is preferably maintained along the length of the drift tube or ion mobility separator 12. The axial DC electric field is preferably achieved by applying a series of DC voltages to the stack or series of ring, plate, annular, wire or rod electrodes 17 which preferably form the drift tube, drift region or ion mobility separator 12.

An AC or RF voltage is also preferably applied between neighbouring rings or electrodes 17 in the stack or series of ring, annular or other electrodes 17 in a similar manner to previously described embodiments.

Under the action of an AC or RF electric field ions are preferably radially confined to a region about the central axis of the ring or electrode stack, whilst simultaneously under the action of the axial DC electric field ions are preferably caused to drift to the exit end of the drift tube or ion mobility spectrometer 12.

The confinement of ions due to the AC or RF electric fields applied to the electrodes 17 forming the drift tube or ion mobility separator 12 preferably prevents ions from migrating away from the central axis of the ion mobility separator and being lost to the rings or electrodes 17 or otherwise to the system.

In this embodiment, ions arriving at the exit region of the drift tube or ion mobility separator are preferably drawn into a further vacuum chamber 25 of the mass spectrometer. An AC or RF ion guide 26 is preferably provided in the further vacuum chamber 25 and preferably acts to guide ions into the further housing of the mass spectrometer.

According to this embodiment ions having first been separated in a Field Asymmetric Ion Mobility Spectrometry device are then further separated in an ion mobility separator before being subsequently mass analysed and detected in a mass spectrometer.

Figure 8:
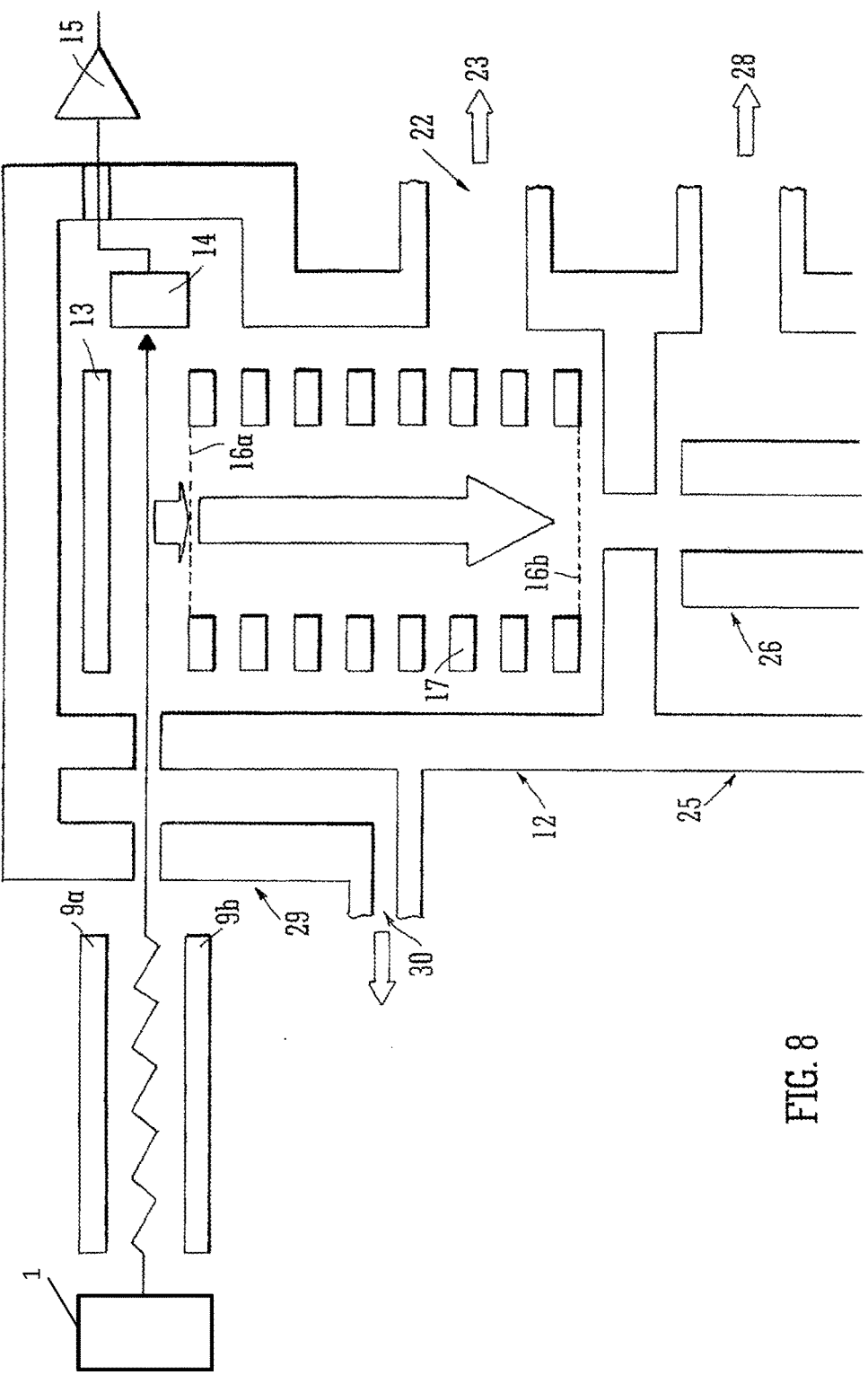
FIG. 8 shows a sixth embodiment of the present invention wherein a FAIMS device is provided in series with an ion mobility separator which forms part of a mass spectrometer and wherein the ion mobility separator is arranged in a vacuum chamber downstream of an initial vacuum chamber.

FIG. 8 shows a sixth embodiment of the present invention and is similar to the fifth embodiment described above with reference to FIG. 7. Ions are produced or generated in an ion source 1. Ions generated in the ion source 1 are preferably directed to pass between two parallel metal electrodes 9a,9b of a Field Asymmetric Ion Mobility Spectrometry or FAIMS device. According to an alternative embodiment the FAIMS device may comprise two concentric cylindrical electrodes or alternative arrangements of electrodes.

At least some of the ions that are transmitted by the FAIMS device are preferably drawn into an initial vacuum chamber 29 of a mass spectrometer. The initial vacuum chamber 29 is preferably evacuated through a port 30.

Ions which enter the initial vacuum chamber 29 are then preferably drawn into another vacuum chamber which is preferably evacuated to a relatively lower pressure than the initial vacuum chamber 29 via a port 22 through which gas 23 is pumped out.

In a mode of operation ions pass on to a plate or ion detector 14 arranged opposed to the entrance of the vacuum chamber housing the drift tube or ion mobility separator 12. An ion current output from the plate or ion detector 14 is preferably amplified by an amplifier 15.

In a mode of operation a voltage is preferably periodically applied to a plate or orthogonal acceleration electrode 13 arranged between the entrance of the vacuum chamber housing the ion mobility separator 12 and the ion detector 14. Ions are preferably orthogonally accelerated by a resultant orthogonal electric field through a first mesh electrode 16a preferably arranged at the entrance to the drift tube or ion mobility separator 12.

An axial DC electric field is preferably maintained along the electrodes 17 forming the drift tube or ion mobility separator 12. The axial DC electric field is preferably maintained by applying a series of DC voltages to the stack or series of ring, annular, wire, plate or rod electrodes 17 forming the ion mobility separator 12.

An AC or RF voltage is also preferably applied between neighbouring rings or electrodes 17 in the stack or series of ring, annular, plate, wire or rod electrodes 17. Under the action of the AC or RF electric field ions are preferably confined to the region about the central axis of the stack or series of ring, annular, plate, wire or rod electrodes 17 whilst simultaneously under the action of the applied axial DC electric field the ions are preferably caused to drift to the exit end of the drift tube or ion mobility separator 12.

The radial confinement of ions due to the applied AC or RF electric field preferably prevents ions from migrating away from the central axis and being lost to the rings or electrodes 17 or otherwise to the system.

In this embodiment, ions arriving at the exit of the drift tube or ion mobility separator 12 are then preferably drawn into a further vacuum chamber 25 of the mass spectrometer. The further vacuum chamber 25 preferably comprises an AC or RF ion guide 26.

According to this embodiment, ions having first been separated in a Field Asymmetric Ion Mobility Spectrometry device are then preferably further separated in an ion mobility separator before being subsequently mass analysed and detected in a mass spectrometer.

Figure 9:
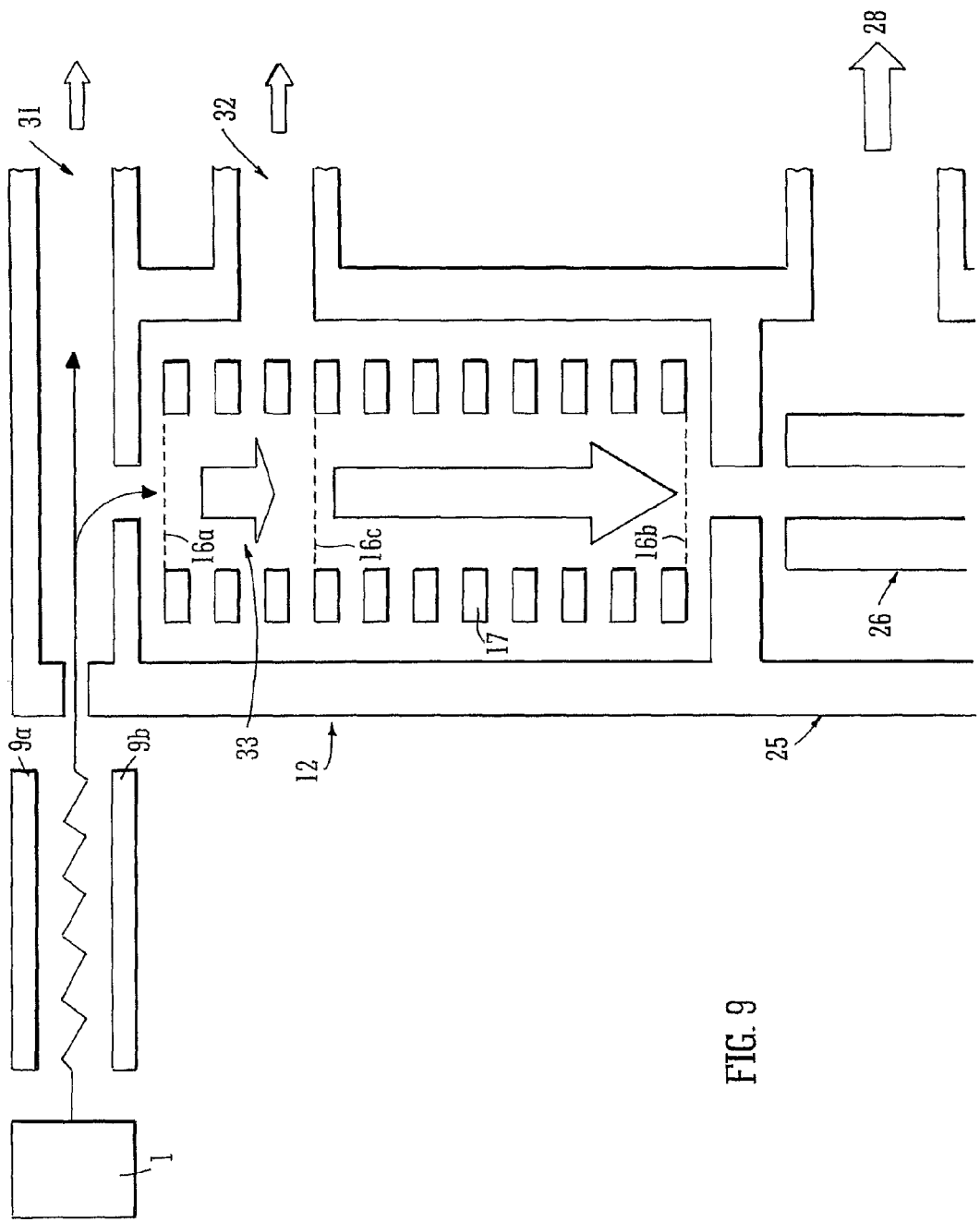
FIG. 9 shows a seventh embodiment of the present invention wherein a FAIMS device is provided in series with an ion mobility separator which forms part of a mass spectrometer and wherein ions are drawn into the ion mobility separator from an initial vacuum chamber.

FIG. 9 shows a seventh embodiment of the present invention which is similar to the sixth embodiment as described above with reference with FIG. 8. Ions are produced or generated in an ion source 1. Ions generated in the ion source 1 are directed to pass between two parallel metal electrodes 9a,9b of a Field Asymmetric Ion Mobility Spectrometry ("FAIMS") device although according to an alternative embodiment the FAIMS device may comprise two concentric cylindrical electrodes or alternative arrangements or electrodes. Ions that are transmitted by the FAIMS device are preferably drawn into an initial vacuum chamber of a mass spectrometer that is preferably evacuated via a port 31. At least some ions are then preferably drawn into a further vacuum chamber comprising a drift tube or ion mobility separator 12. The further vacuum chamber is preferably evacuated to a relatively lower pressure via a vacuum port 32.

Ions entering this further vacuum chamber may be collected and stored in an ion trapping region 33 provided in an initial region of the drift tube or ion mobility spectrometer. The ion trapping region is preferably created by applying trapping voltages to either a first mesh electrode 16a arranged at the entrance to the drift tube or ion mobility separator 12 and/or to a third mesh electrode 16c arranged downstream from the first mesh electrode 16a and part way along the length of the drift tube or ion mobility separator 12.

The ion trapping region 33 preferably comprises a series of electrodes, preferably substantially similar to the electrodes 17 forming the main body of the drift tube or ion mobility separator 12.

An AC or RF voltage is preferably applied between neighbouring electrodes in the upstream ion trapping region 33 of the drift tube or ion mobility separator 12 and/or to the electrodes 17 forming the main body of the drift tube or ion mobility separator 12. The AC or RF voltage preferably acts to confine ions close to a central axis of the drift tube or ion mobility separator 12.

At the exit end or region of the ion trapping region 33 an electrode, preferably a further (third) mesh electrode 16c, with an appropriate DC voltage applied, is preferably used to trap ions within the ion trapping region 33. The voltage at which the further (third) mesh electrode 16c is maintained may be periodically pulsed to a lower voltage in order to allow a packet of ions to pass out of the trapping region 33 and into the drift tube or main body of the ion mobility separator 12.

The voltage applied to the third mesh electrode 16c may be reset and hence further ions may be accumulated and trapped in the ion trapping region 33. The further ions may arrive in the ion trapping region 33 substantially continuously whilst the previous packet of ions are being separated according to their ion mobility and/or subsequently analysed.

Ions that are caused to exit the ion trapping region 33 preferably pass into the drift tube or ion mobility separator 13. An axial DC electric field is preferably maintained along the length of the drift tube or ion mobility separator 12. The axial DC electric field is preferably maintained by applying a series of DC voltages to the stack or series of ring, annular, plate, wire or rod electrodes 17 which comprise the drift tube or ion mobility separator 12.

An AC or RF voltage is preferably also applied between neighbouring rings or electrodes 17 in the stack or series of ring, annular, plate, wire or rod electrodes 17 forming the drift tube or ion mobility separator 12. Under the action of the AC or RF electric field the ions are preferably confined to a region about the central axis of the ring stack or ion mobility separator 12 whilst simultaneously under the action of the axial DC electric field the ions are preferably caused to drift to the exit end of the drift tube or ion mobility separator 12.

The confinement due to the AC or RF electric field preferably prevents ions from migrating away from the central axis of the trapping region 32 and/or the drift tube or ion mobility separator 12 and being lost to the electrodes 17 or otherwise to the system.

In this embodiment, ions arriving at the exit of the drift tube or ion mobility separator are preferably drawn into a further vacuum chamber 25 of the mass spectrometer. The further vacuum chamber 25 preferably comprises an AC or RF ion guide.

According to this embodiment ions having first been separated in a FAIMS device are preferably further separated in an IMS device or ion mobility drift tube. The ions are then subsequently mass analysed and detected in a mass spectrometer.

According to further embodiments which are equally applicable to all the embodiments described above in addition to or instead of applying or maintaining a constant axial DC voltage gradient along the length of the ion mobility separator or spectrometer a time varying voltage gradient may be applied. In particular, one or more transient DC voltages or one or more transient DC voltage waveforms may be progressively applied to the electrodes forming the drift tube or the ion mobility separator so that at least some ions having a first ion mobility are separated from other ions having a second different ion mobility.

Although the present invention has been described with reference to preferred embodiments, it will be understood by those skilled in the art that various changes in form and detail may be made without departing from the scope of the invention as set forth in the accompanying claims.

The invention claimed is:

1. An apparatus comprising:
a first device for separating ions according to their rate of change of ion mobility with electric field strength, said first device comprising a Field Asymmetric Ion Mobility Spectrometry ("FAIMS") device with a central axis;
a second device for separating ions according to their ion mobility, said second device comprising an ion mobility separator or ion mobility spectrometer, and said second device being arranged downstream of said first device along a central axis that is substantially orthogonal to the central axis of said first device;
an acceleration electrode for substantially orthogonally accelerating ions leaving the first device into the second device;
wherein the second device comprises an entrance region and a mesh electrode located in the entrance region wherein, in use, an electric field is maintained between the acceleration electrode and the mesh electrode and accelerates the ions leaving the first device through the mesh electrode, and
wherein said second device comprises a plurality of electrodes and wherein, in use, one or more transient DC voltages or one or more transient DC voltage waveforms are progressively applied to said plurality of electrodes so that at least some ions having a first ion mobility are separated from other ions having a second different ion mobility.

2. The apparatus as claimed in claim 1, wherein said first device comprises at least a first electrode and a second electrode and wherein ions are arranged to be received, in use, between said first and second electrodes.

3. The apparatus as claimed in claim 1, further comprising an asymmetric periodic voltage waveform applied to said first device, wherein said asymmetric periodic voltage waveform has a peak positive voltage and a peak negative voltage.

4. The apparatus as claimed in claim 1, further comprising a DC compensation voltage applied to said first device.

5. The apparatus as claimed in claim 4, wherein said DC compensation voltage acts to counterbalance or counteract a force which would otherwise cause desired ions to drift towards an electrode of said first device.

6. The apparatus as claimed in claim 1, wherein said second device is selected from the group consisting of: (i) an ion funnel comprising a plurality of electrodes having apertures therein through which ions are transmitted, wherein the diameter of said apertures becomes progressively smaller or larger; (ii) an ion tunnel comprising a plurality of electrodes having apertures therein through which ions are transmitted, wherein the diameter of said apertures remains substantially constant; and (iii) a stack of plate, ring or wire loop electrodes.

7. The apparatus as claimed in claim 1, wherein said second device comprises a segmented rod set.

8. The apparatus as claimed in claim 1, wherein an AC or RF voltage is applied to at least some of said electrodes of said second device in order to confine at least some ions, in use, near to a central axis of said second device.

9. The apparatus as claimed in claim 1, wherein one or more DC voltage gradients are maintained across at least a portion of said second device.

10. The apparatus as claimed in claim 1, wherein said one or more transient DC voltages or said one or more transient DC voltage waveforms are such that at least 10%, 20%, 30%, 40%, 50%, 60%, 70%, 80%, 90% or 95% of said ions having said second ion mobility are moved along said second device by said applied DC voltage to a lesser degree than said ions having said first ion mobility as said one or more transient DC voltages or said one or more transient DC voltage waveforms are progressively applied to said electrodes.

11. The apparatus as claimed in claim 1, wherein one or more transient DC voltages or one or more transient DC voltage waveforms are progressively applied to said electrodes so that ions are moved towards a region of the ion mobility separator wherein at least one electrode has a potential such that at least some ions having a first ion mobility will pass across said potential whereas other ions having a second different ion mobility will not pass across said potential.

12. The apparatus as claimed in claim 11, wherein said one or more transient DC voltages or said one or more transient DC voltage waveforms are such that at least 10%, 20%, 30%, 40%, 50%, 60%, 70%, 80%, 90% or 95% of said ions having said first ion mobility pass across said potential.

13. The apparatus as claimed in claim 11, wherein said one or more transient DC voltages or said one or more transient DC voltage waveforms are such that at least 10%, 20%, 30%, 40%, 50%, 60%, 70%, 80%, 90% or 95% of said ions having said second ion mobility will not pass across said potential.

14. The apparatus as claimed in claim 1, wherein said one or more transient DC voltages applied to said second device create: (i) a potential hill or barrier; (ii) a potential well; (iii) a combination of a potential hill or barrier and a potential well; (iv) multiple potential hills or barriers; (v) multiple potential wells; or (vi) a combination of multiple potential hills or barriers and multiple potential wells.

15. The apparatus as claimed in claim 1, wherein said one or more transient DC voltage waveforms comprise a repeating waveform.

16. The apparatus as claimed in claim 1, wherein ions are confined radially within said first device or said second device by an AC or RF electric field.

17. The apparatus as claimed in claim 1, wherein one or more transient DC voltages or one or more transient DC voltage waveforms move from one end of said first device or said second device to another end of said first device or said second device so that at least some ions are urged along said first device or said second device.

18. The apparatus as claimed in claim 1, wherein said first device or said second device comprises an upstream entrance region, a downstream exit region and an intermediate region, wherein:

in said entrance region the amplitude of said one or more transient DC voltages or said one or more transient DC voltage waveforms has a first amplitude;

in said intermediate region the amplitude of said one or more transient DC voltages or said one or more transient DC voltage waveforms has a second amplitude; and in said exit region the amplitude of said one or more transient DC voltages or said one or more transient DC voltage waveforms has a third amplitude.

19. The apparatus as claimed in claim 18, wherein said first or third amplitudes are substantially zero and said second amplitude is substantially non-zero.

20. The apparatus as claimed in claim 1, wherein two or more transient DC voltages or two or more transient DC voltage waveforms are applied to said first device or said second device and pass simultaneously along said first device or said second device.

21. The apparatus as claimed in claim 20, wherein said two or more transient DC voltages or said two or more transient DC voltage waveforms are arranged to move: (i) in the same direction; (ii) in opposite directions; (iii) towards each other; or (iv) away from each other.

22. The apparatus as claimed in claim 1, wherein one or more transient DC voltages or one or more transient DC voltage waveforms pass along said first device or said second device and at least one substantially stationary transient DC potential voltage or voltage waveform is provided at a position along said first device or said second device.

23. The apparatus as claimed in claim 1, wherein in use pulses of ions emerge from an exit of said first device or said second device.

24. The apparatus as claimed in claim 23, further comprising an ion detector, said ion detector being arranged to be substantially phase locked in use with the pulses of ions emerging from the exit of said first device or said second device.

25. The apparatus as claimed in claim 23, further comprising a Time of Flight mass analyser comprising an electrode for injecting ions into a drift region, said electrode being arranged to be energised in use in a substantially synchronised manner with the pulses of ions emerging from the exit of the first device or said second device.

26. The apparatus as claimed in claim 1, wherein said first device or said second device comprise a plurality of electrodes and wherein at least 10%, 20%, 30%, 40%, 50%, 60%, 70%, 80%, 90%, or 95% of said electrodes are connected to both a DC and an AC or RF voltage supply.

27. The apparatus as claimed in claim 1, further comprising a continuous ion source.

28. The apparatus as claimed in claim 1, further comprising a pulsed ion source.

29. The apparatus as claimed in claim 1, further comprising an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source.

30. The apparatus as claimed in claim 1, further comprising a separation device for separating a sample to be analysed prior to ionisation.

31. The apparatus as claimed in claim 30, wherein said separation device is selected from the group consisting of: (i) a liquid chromatography device; (ii) a gas chromatography device; (iii) a super-critical fluid chromatography device; (iv) a capillary electrophoresis device; and (v) a capillary electrophoresis chromatography device.

32. A mass spectrometer comprising the apparatus as claimed in claim 1.

33. The mass spectrometer as claimed in claim 32, further comprising a mass analyser.

34. The mass spectrometer as claimed in claim 33, wherein said mass analyser is selected from the group consisting of: (i) an orthogonal acceleration Time of Flight mass analyser; (ii) an axial acceleration Time of Flight mass analyser; (iii) a Paul 3D quadrupole ion trap mass analyser; (iv) a 2D or linear quadrupole ion trap mass analyser; (v) a Fourier Transform Ion Cyclotron Resonance mass analyser; (vi) a magnetic sector mass analyser; (vii) a quadrupole mass analyser; and (viii) a Penning trap mass analyser.

35. The mass spectrometer as claimed in claim 32, further comprising a collision or fragmentation cell.

36. The apparatus as claimed in claim 1, further comprising an ion detector arranged downstream of the first device to detect ions exiting said first device when the acceleration electrode is not accelerating the ions.

37. The apparatus as claimed in claim 1, wherein said acceleration electrode is arranged downstream of the first device and upstream of the second device.

38. A method of separating ions comprising:
separating ions according to their rate of change of ion mobility with electric field strength in a first device, said first device comprising a Field Asymmetric Ion Mobility Spectrometry ("FAIMS") device;
pulsing an acceleration electrode arranged between the first device and a second device to accelerate ions leaving the first device substantially orthogonally through a mesh electrode located in an entrance region of said second device into the second device; and then
separating ions according to their ion mobility in a second device, said second device comprising an ion mobility separator or ion mobility spectrometer having a plurality of electrodes, and said second device being arranged downstream of said first device;
wherein said step of separating ions in said second device comprises progressively applying to said electrodes one or more transient DC voltages or one or more transient DC voltage waveforms so that at least some ions having a first ion mobility are separated from other ions having a second different ion mobility.

39. A method of mass spectrometry comprising the method of claim 38.

40. The method according to claim 38 further comprising:
directly detecting ions leaving the first device with an ion detector when the acceleration electrode is not being pulsed.

41. The method according to claim 38 further comprising:
selectively pulsing the acceleration electrode to selectively provide data from the first device or combined data from both the first and second device; and periodically pulsing the acceleration electrode to provide data from the first device and combined data from both the first and second device virtually simultaneously.

42. An apparatus comprising:
a first device for separating ions according to their rate of change of ion mobility with electric field strength, said first device comprising a Field Asymmetric Ion Mobility Spectrometry ("FAIMS") device with a central axis;
a second device for separating ions according to their ion mobility, said second device comprising an ion mobility separator or ion mobility spectrometer, and said second device being arranged downstream of said first device along a central axis that is substantially orthogonal to the central axis of said first device;
an acceleration electrode for substantially orthogonally accelerating ions leaving the first device into the second device;
wherein the second device comprises an entrance region and a mesh electrode located in the entrance region wherein, in use, an electric field is maintained between the acceleration electrode and the mesh electrode and accelerates the ions leaving the first device through the mesh electrode, and
wherein said second device comprises a plurality of electrodes, each electrode having an aperture through which ions are transmitted in use, and wherein an AC or RF voltage is applied to at least some of said electrodes of said second device in order to confine at least some ions, in use, near to a central axis of said second device.

43. A mass spectrometer comprising the apparatus as claimed in claim 42.

44. The apparatus as claimed in claim 42, further comprising an ion detector arranged downstream of the first device to detect ions exiting said first device when the acceleration electrode is not accelerating the ions.

45. A method of separating ions comprising:
separating ions according to their rate of change of ion mobility with electric field strength in a first device, said first device comprising a Field Asymmetric Ion Mobility Spectrometer ("FAIMS") device;
pulsing an acceleration electrode arranged between the first device and a second device to accelerate ions leaving the first device substantially orthogonally through a mesh electrode located in an entrance region of said second device into the second device; and then
separating ions according to their ion mobility in a second device, said second device comprising an ion mobility separator or ion mobility spectrometer having a plurality of electrodes, each electrode having an aperture through which the ions are transmitted, and said second device being arranged downstream of said first device;
wherein an AC or RF voltage is applied to at least some of the electrodes of said second device so as to confine at least some of the ions in said second device near to a central axis of the second device.

46. A method of mass spectrometry comprising the method of claim 45.

47. The method according to claim 45 further comprising:
directly detecting ions leaving the first device with an ion detector when the acceleration electrode is not being pulsed.

* * * * *